(12) United States Patent
Altel et al.

(10) Patent No.: US 12,157,745 B2
(45) Date of Patent: Dec. 3, 2024

(54) HETEROCYCLIC SYSTEMS AND PHARMACEUTICAL COMPOSITIONS THEREOF

(71) Applicant: University of Sharjah, Sharjah (AE)

(72) Inventors: Taleb H. Altel, Sharjah (AE); Raafat A El-Awady, Sharjah (AE); Srinivasulu Vunnam, Sharjah (AE); Cijo George Vazhappilly, Sharjah (AE); Hany A. Omar, Sharjah (AE)

(73) Assignee: UNIVERSITY OF SHARJAH, Sharjah (AE)

( * ) Notice: Subject to any disclaimer, the term of this patent is extended or adjusted under 35 U.S.C. 154(b) by 0 days.

(21) Appl. No.: 17/112,088

(22) Filed: Dec. 4, 2020

(65) Prior Publication Data

US 2021/0221825 A1    Jul. 22, 2021

Related U.S. Application Data

(63) Continuation of application No. 15/935,155, filed on Mar. 26, 2018, now abandoned.

(51) Int. Cl.
| | |
|---|---|
| *C07D 513/14* | (2006.01) |
| *A61P 35/00* | (2006.01) |
| *C07D 471/14* | (2006.01) |
| *C07D 471/22* | (2006.01) |
| *C07D 491/147* | (2006.01) |
| *C07D 513/22* | (2006.01) |

(52) U.S. Cl.
CPC ............ *C07D 513/14* (2013.01); *A61P 35/00* (2018.01); *C07D 471/14* (2013.01); *C07D 471/22* (2013.01); *C07D 491/147* (2013.01); *C07D 513/22* (2013.01)

(58) Field of Classification Search
CPC .................................................. C07D 513/14
See application file for complete search history.

(56) References Cited

PUBLICATIONS

Vunnam Srinivasulu, "Intramolecular Diaza-Diels-Alder Protocol: A New Diastereoselective and Modular One-Step Synthesis of Constrained Polycyclic Frameworks", Journal, 2017, 4137-4148, Chemistry—A European Journal.

*Primary Examiner* — Brian E McDowell
(74) *Attorney, Agent, or Firm* — MH2 TECHNOLOGY LAW GROUP, LLP

(57) ABSTRACT

A compound represented by following formula I:

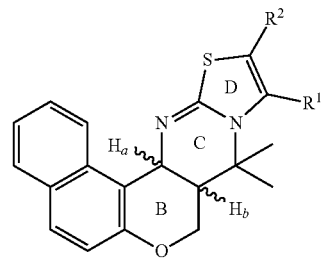

according to the present disclosure. The disclosed compound is useful in the treatment of many disease states related to cell proliferation. In particular, new pyran derivatives are provided along with processes for preparations and methods for pharmaceutical applications, for example, as anticancer agents. The compound was found to have antiproliferative effects against multiple cancer cell lines and showed low toxicity to normal fibroblasts. The disclosed compound also exhibited anticancer properties by inducing caspase-mediated cell death mechanisms and arresting cancer cell progression. Further, the compound represented by Formula I targets multiple key proteins/enzymes, including thioredoxin reductase, glutathione reductase, transferrin receptors, inisitol-3-phosphate synthase, cystolic aminopeptidase, and transketolase, which are over-expressed in tumor cells.

7 Claims, 15 Drawing Sheets

HETEROCYCLIC SYSTEMS AND PHARMACEUTICAL COMPOSITIONS THEREOF

CROSS-REFERENCE TO RELATED APPLICATIONS AND PRIORITY

This patent application claims priority from U.S. patent application Ser. No. 15/935,155 filed Mar. 26, 2018, the contents of which are herein incorporated by reference in their entirety.

FIELD OF THE INVENTION

This disclosure relates to novel antitumor agents, pharmaceutically acceptable salts thereof, as well as processes of manufacture, and medicaments containing such compounds. The presently disclosed compounds have anticancer activity, which results in reduction of tumor cell proliferation, induction of apoptosis, as well as DNA damage. This present disclosure also concerns the use of the disclosed compounds in relation to the enzymes thioredoxin reductase, transketolase, cytosol aminopeptidase, glutathione reductase, inositol-3-phosphate synthase, and transferrin receptor activities in addition to regulation of these enzymes.

BACKGROUND

Rising incident rates of cancer and challenges like multi-drug resistance and side effects possessed by existing classes of anticancer drugs encourage researchers to develop new compounds with potential anticancer activities and newer modes of action. In this regard, phenotype-based screening of diverse compound collections generated by privileged substructure-based diversity-oriented synthesis (pDOS) is considered one of the prominent approaches in the discovery of novel drug leads. Indeed, pDOS is an attractive technique to synthesize small molecules collections with chemical scaffolds that frequently exist in natural products as well as drugs that can target previously unexploited features of disease-relevant proteins.

SUMMARY

A benzopyran skeleton and analogs thereof constitute the core scaffold of many bioactive natural products and synthetic drugs. For instance, the microglial inhibitor P24A01 and P23C07, a potent antitumor agent, have been discovered using the pDOS approach. Other important examples of biologically significant compounds containing benzopyran as the core skeleton are tephrosin, deguelin, acronycine, 5-HT-3 receptor antagonist, tetrahydrocannabinol, metachromin T, and daleformis. There has been a growing interest in these scaffolds and novel and modular routes to access these scaffolds in a one pot reaction manner with good overall yields are described herein. Additionally, there is a continuous need in the art to identify novel compounds useful in the treatment of disease states and the present disclosure introduces novel heterocyclic fused polycyclic systems as pharmaceutically useful compounds for this and other possible purposes.

Specifically, this disclosure relates to novel antitumor agents and pharmaceutically acceptable salts thereof, processes for the manufacture of these novel constrained polycyclic benzopyran frameworks, and medicaments containing such compounds. In some embodiments, the disclosed polycyclic benzopyrans have a general formula of A or B, as provided herein and described in detail below:

General Formula A

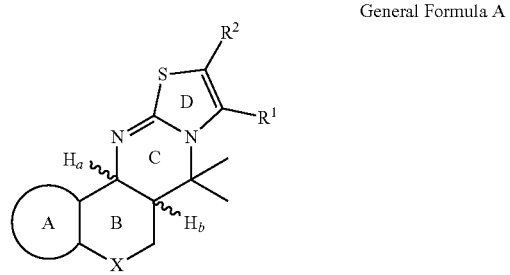

General Formula B

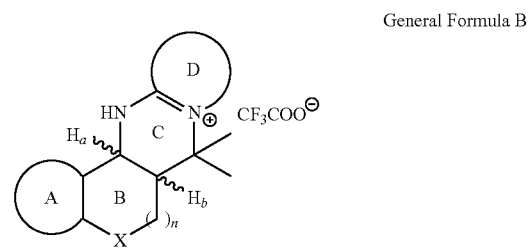

The presently disclosed compounds may, in some embodiments, have anticancer activity, which results in inhibition of tumor cell proliferation, induction of apoptosis, as well as DNA damage. As described below in detail, the present disclosure also includes the use of such compounds in relation to key enzymes, such as thioredoxin reductase, transketolase, cytosol aminopeptidase, glutathione reductase, inositol-3-phosphate synthase, and/or transferrin receptor proteins.

The subject disclosure provides novel constrained polycyclic compounds of general formula A as well as pharmaceutical acceptable salts thereof, methods of preparing these compounds, and uses of such novel compounds for different disease states, including but not limited to, cell proliferative diseases and diseases related to thioredoxin reductase, transketolase, cytosol aminopeptidase, glutathione reductase, inositol-3-phosphate synthase, transferrin receptor proteins, and/or other key proteins.

Some of the disclosed novel constrained polycyclic compounds having the general formula A are further described below. In general formula A:

is an aryl, heteroaryl, alicyclic, or heteroalicyclic ring, which may be unsubstituted or substituted. In embodiments in which

is a substituted ring,

may be substituted with 1, 2, 3, or 4 substituents, which may be independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$, wherein $R^3$ is hydrogen or, optionally, a substituted group selected from the group consisting of: a C1-6 aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

X is —O, —$NR^4$, —$NSO_2R^4$, —$CH_2$, —$CHR^4$, or —$C(R^4)_2$, wherein $R^4$ is selected from the group consisting of: hydrogen, an unsubstituted or a substituted alkyl, aryl, or heteroaryl group; and $H_a$ and $H_b$ are each hydrogen atoms.

In some embodiments, $R^1$ and $R^2$ are each independently selected from the group consisting of: a hydrogen atom, a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$. However, in other embodiments, $R^1$ and $R^2$ are connected to form a 5 or 6 membered ring which is fused to ring D. In these and other embodiments, the 5 or 6 membered rings are either unsubstituted or substituted with 1, 2, 3, or 4 substituents, which may be independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$.

In another aspect, the subject disclosure provides novel constrained polycyclic compounds of the general formula B, along with pharmaceutical acceptable salts thereof, methods of preparing these compounds, and uses of such novel compounds for the treatment of different disease states, including but not limited to cell proliferative diseases and diseases that are related to thioredoxinreductase activity and other key enzymes.

In general formula B:

is an aryl, heteroaryl, alicyclic, or heteroalicyclic ring, which may be unsubstituted or substituted with 1, 2, 3, or 4 substituents that may independently be selected from the group consisting of: a halogen atom, CN, $R^1$, $OR^1$, $SR^1$, $N(R^1)_2$, $C(O)R^1$, $C(O)OR^1$, $NR^1C(O)R^1$, $C(O)NR^1$, $SO_2R^1$, $NR^1SO_2R^1$, and $SO_2N(R^1)_2$, wherein $R^1$ is hydrogen or a substituted group selected from the group consisting of: a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

X is selected from the group consisting of: —O, —$NR^2$, —$NSO_2R^2$, —$CH_2$, —$CHR^2$, and —$C(R^2)_2$, wherein $R^2$ is hydrogen or an unsubstituted or substituted alkyl, aryl, or heteroaryl group;

$H_a$ and $H_b$ are each hydrogen atoms;

n=1, 2, or 3, thereby providing ring B with 6, 7, or 8 members, respectively; and

is a 5, 6, or 7 membered heterocyclic ring, which may be unsubstituted or substituted with 1, 2, 3, or 4 substituents independently selected from the group consisting of: a halogen atom, CN, $R^1$, $OR^1$, $SR^1$, $N(R^1)_2$, $C(O)R^1$, $C(O)OR^1$, $NR^1C(O)R^1$, $C(O)NR^1$, $SO_2R^1$, $NR^1SO_2R^1$, and $SO_2N(R^1)_2$.

In a further embodiment, the subject disclosure provides novel synthetic methods for the preparation of compounds of the general formula A and B and pharmaceutical compositions thereof. Compounds of general formula A can be prepared according to any of the techniques described below in addition to other techniques. For example, in some embodiments, a condensation reaction is followed by an intramolecular Diels-Alder reaction between the compounds of general formula I and II to yield compounds of general formula A.

General formula I

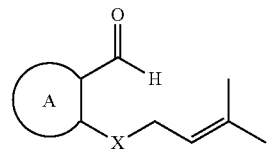

General formula II

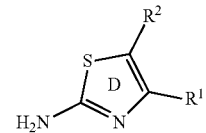

In general formulas I and II,

X, $R^1$ and $R^2$ are as previously described herein.

Compounds of general formula B can be prepared according to any suitable technique. For example, in some example embodiments, a condensation reaction followed by an intramolecular Diels-Alder reaction between the compounds of general formula III and IV is used to produce compounds of the general formula B.

General formula III

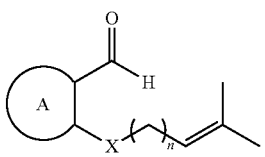

General formula IV

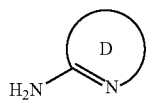

In general formulas III and IV,

,

X, and

are as previously described.

Additionally, the subject disclosure also provides pharmaceutical compositions comprising compounds of general formulas A and B.

In another aspect, the present disclosure provides methods of screening anticancer agents by treating a subject suffering from or susceptible to cancer or a different condition mediated by continuous cell proliferation. The disclosed methods of treatment include, in some embodiments, administering to a subject an effective amount of a compound or pharmaceutical composition described herein.

In yet another aspect, the present disclosure provides methods of analyzing the cell cycle arresting potentials and/or apoptosis in a biological system by administering to a subject or contacting a biological system with an effective amount of one or more disclosed compounds.

In a further aspect, the present disclosure describes the ability of the disclosed compounds to disturb cell polymerization dynamics by tubulin formation, which is necessary for cancer cell division.

In another aspect, the present disclosure relates to the potential of the disclosed compounds to target caspase-3 mediated apoptotic mechanisms present in aggressive forms of breast cancer cells.

In yet another aspect, the present disclosure provides a platform capable of disturbing the DNA of cancerous cells and inducing the expression of DNA damage marker proteins in aggressive SKBR-3 cells in an ATR-Chk2 dependent manner.

In another aspect, the present disclosure provides methods of inhibiting thioredoxin reductase 1 (TrxR 1) in a subject or a biological system by administering to the subject or contacting the biological system with an effective amount of one or more compounds disclosed herein.

DETAILED DESCRIPTION

Figure 1:
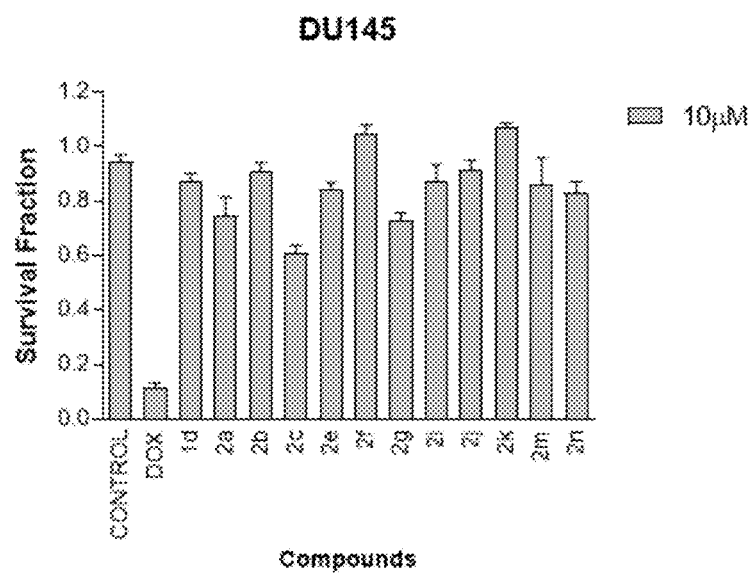
FIG. 1 is a chart showing anti-proliferative effects of various compounds on survival of prostate cancer cells DU-145, in accordance with some embodiments of the subject disclosure.

This disclosure provides novel heterocyclic fused constrained ring systems of the general formulas A and B, methods of preparing these systems, and the use of such novel compounds for different disease states, such as treatment agents for cell proliferative diseases. When discussing such compounds and compositions the following terms have the following meaning unless otherwise indicated.

As used herein, the term "aryl" means an aromatic or partially aromatic hydrocarbon group containing 6 to 10 carbon atoms and consisting of one or two rings which may be fused to each other or attached to each other via a single bond. Examples of "aryl" groups include phenyl, napthyl, biphenyl, and indenyl groups.

The term "heteroaryl," as used herein, means an aromatic or partially aromatic group consisting of one or two rings, which may be fused to each other or attached to each other via a single bond, and containing 5 to 10 ring atoms wherein up to four (e.g., one, two, three, or four) ring atoms are heteroatoms and the remaining ring atoms are carbon. Examples of heteroaryl groups include but are not limited to: pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The term "alicyclic" means a saturated or unsaturated aliphatic cyclic ring system consisting of one or more rings, which may be fused to each other or attached to each other via a single bond, and containing 5 to 10 ring atoms, such as carbon atoms. Example alicyclic groups include cyclopentane, cyclohexane, cycloheptane, cyclooctane, and terpene groups.

The term "heteroalicyclic" refers to any five to seven membered monocyclic, saturated, or partially unsaturated ring structure containing at least one heteroatom selected from the group consisting of O, N, and S, optionally containing one to three additional heteroatoms independently selected from the group consisting of O. N, and S, or a nine to ten membered saturated, partially unsaturated, partially aromatic bicyclic or spiro-fused ring system containing at least one heteroatom selected from the group consisting of O, N, and S, and optionally containing one to four additional heteroatoms independently selected from the group consisting of O. N, and S. Examples of heteroalicyclic groups include but are not limited to: pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, 2-aza-spiro[4.5]decyl, and the like. In some cases, a heterocycloalkyl group may be attached at any heteroatom or carbon atom of a heteroalicyclic ring.

The term "alkyl," as used herein, denotes a saturated, linear, or branched chain hydrocarbon group containing 1 to 8 carbon atoms, for example 1 to 6 or 1 to 4 carbon atoms, such as methyl, ethyl, propyl, isopropyl, 1-butyl, 2-butyl, tert-butyl, and the like. Some particular "C1-C8 alkyl" groups have 1, 2, or 3 carbon atoms.

The term "halogen" means fluorine, chlorine, bromine, or iodine.

The term "substituted" means a group which may be substituted one to three times by a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and/or $SO_2N(R^3)_2$.

With reference to substituents, the term "independently" means that when more than one of such substituents is possible, such substituents may be the same or different from each other.

The term "pharmaceutically acceptable salt" refers to conventional acid-addition salts or base-addition salts that retain the biological effectiveness and properties of the compounds of the disclosed chemical formulas and are formed from suitable non-toxic organic or inorganic acids or organic or inorganic bases. Acid-addition salts include, for example, those derived from inorganic acids, such as hydrochloric acid, hydrobromic acid, hydroiodic acid, sulfuric acid, sulfamic acid, phosphoric acid, and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium, and quaternary ammonium hydroxides, such as for example, tetramethyl ammonium hydroxide.

The term "polar-aprotic solvent" means a polar solvent which does not contain acidic hydrogen and does not act as a hydrogen bond donor. Examples of polar-aprotic solvents include dimethylsulfoxide, dimethylformamide, hexamethylphosphorotriamide, n-methyl pyrrolidone, tetrahydrofuran, and ACN.

The presently disclosed compounds can possess one or more asymmetric (or chiral) carbon atoms and are thus capable of existing in the form of optical isomers as well as in the form of racemic or non-racemic mixtures thereof. In some embodiments, the disclosed compounds are used in the form of pure enantiomers, diastereoisomers, or racemic mixtures. The disclosed isomeric compounds can be utilized as a single isomer or as a mixture of stereochemical isomeric forms. Diastereoisomers, i.e., nonsuperimposable stereochemical isomers, can be separated by conventional means, such as chromatography, distillation, crystallization, or sublimation. Optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric, and camphorsulfonic acid. A mixture of diastereomers can be separated by crystallization followed by liberation of the optically active bases from these salts. An alternative process for separation of optical isomers includes the use of a chiral chromatography column optimally chosen to maximize the separation of the enantiomers.

The pro-drugs to which the present disclosure also relates include one or more compounds of the formula A and/or B and at least one pharmacologically acceptable protecting group which will be removed under physiological conditions, such as, for example, an alkoxy-, aralkyloxy-, acyl- or acyloxy group, such as an ethoxy, benzyloxy, acetyl, or acetyloxy group.

The present disclosure also relates to the disclosed compounds as active ingredients in the preparation of medicaments. In general, compounds of the formula A and/or B may be administered either individually, or in combination with any other desired therapeutic agent, using known and acceptable methods. Such therapeutically useful agents may be administered, for example, by one of the following routes: orally, for example, in the form of dragees, coated tablets, pills, semi-solid substances, soft or hard capsules, solutions, emulsions, or suspensions; parenterally, for example, in the form of an injectable solution; rectally in the form of suppositories; by inhalation, for example, in the form of a powder formulation or a spray; and/or transdermally or intranasally. For the preparation of such tablets, pills, semi-solid substances, coated tablets, dragees, and hard gelatin capsules, the therapeutically usable product may be mixed with pharmacologically inert, inorganic or organic pharmaceutical carrier substances, for example, lactose, sucrose, glucose, gelatin, malt, silica gel, starch, or derivatives thereof, talcum, stearic acid or salts thereof, skimmed milk powder, and/or the like. For the preparation of soft capsules, pharmaceutical carrier substances, such as, for example, vegetable oils, petroleum, animal, or synthetic oils, wax, fat, and polyols may be used. For the preparation of liquid solutions and syrups, pharmaceutical carrier substances, such as, for example, water, alcohols, aqueous saline solution, aqueous dextrose, polyols, glycerol, vegetable oils, petroleum, and animal or synthetic oils may be used. For suppositories, pharmaceutical carrier substances, such as, for example, vegetable oils, petroleum, animal or synthetic oils, wax, fat, and/or polyols may be used. For aerosol formulations, compressed gases that are suitable for this purpose, such as, for example, oxygen, nitrogen, and/or carbon dioxide may be used. The pharmaceutically acceptable agents may also comprise additives for preserving and stabilizing, emulsifiers, sweeteners, flavorings, salts for altering the osmotic pressure, buffers, encapsulation additives, and/or antioxidants, in some embodiments.

As used herein with reference to the disclosed compounds, methods of use, and efficacy for treating cancer and related conditions, the following terms have the provided meaning, unless otherwise stated.

The term "anticancer" defines the use of natural/synthetic methods/substances for effective health care to contribute to and/or prevent the uncontrolled proliferation of tumor cells.

In certain aspects, the term "breast cancer" refers to a condition that develops in breast tissue. Signs of breast cancer may include a lump in the breast, a change in breast shape, dimpling of the skin, fluid coming from the nipple, and/or a red scaly patch of skin.

The term "proliferative" or "proliferation" in biological conditions refers to uncontrolled multiplication due to failure in normal functioning of a system or a cell.

The term "drug" refers to a natural or synthetic substance which (when administered to a living body) affects its functioning or structure, and is used in the diagnosis, mitigation, treatment, prevention of disease, and/or or relief from discomfort.

The term "multi-drug resistance" (MDR) refers to the condition wherein the effect of a drug will be compromised and will not be effective further. MDR may, in some cases, act as a prognostic factor in tumor relapse.

The term "effective amount" when used in connection with a compound of the general formulas A and/or B means an amount of the subject compound effective for treating or preventing cancer or any other related or unrelated disease(s).

The term "full dose-response curve" is used herein with respect to multiple dosages of a compound to determine its response on a biological system, such as a cell-based model, to study the structural and functional relationship of a compound.

The term "microtubule" denotes the microscopic tubular structure present inside the cytoplasm of cells, sometimes aggregating to form more complex structures and eukaryotic cells, maintaining their shape and assisting in forming the cell spindle during cell division.

The term "mitosis" refers to a condition wherein the cell divides in to two daughter cells in an organized manner.

The term "apoptosis" refers to programmed cell death that occurs in multicellular organisms in order to sustain life. Apoptosis often characterized by mainly two forms, extrinsic and intrinsic pathways that lead to cell death process. Conventionally, apoptosis is distinct from necrosis.

The term "mitochondria" refers to an organelle present mainly in eukaryotic organism that is often referred to as the metabolic center for life activities of a cell and provides energy for the cell.

The term "cell cycle" relates to the process of cell division or the series of events that take place in a cell leading to its division and duplication of its DNA to produce two daughter cells.

The term "caspase" includes a set of cysteine-aspartic proteases, cysteine aspartases or cysteine-dependent aspartate-directed proteases, belonging to a family of protease enzymes that play an essential role in programmed cell death (including apoptosis, pyroptosis, and necroptosis) and inflammation.

The term "oncogene" defines a set of genes that are mutated and cause cancer by genetic conformational changes by forming proto-oncogenes.

The term "migration" as used in the present disclosure describes the ability of tumor cells to migrate to different part of the body and accumulate and form multiple types of cancer.

The term "DNA damage" refers to a mechanism by which normal DNA is altered either by endogenous or exogenous factors, thereby initiating a series of events that may ultimately lead to DNA breaks and cell death.

The term "DNA crosslink" refers to a condition wherein various exogenous or endogenous agents react with two nucleotides of DNA, forming a covalent linkage between them and regulating the epigenetic mechanism in humans.

As used herein, the following abbreviations have the following stated meanings:
ACN=Acetonitrile
TFA=Trifluoroacetic acid
EtOAc=Ethylacetate
DCM=Dicholoromethane
MeOH=Methanol
NMR=Nuclear magnetic resonance
HRMS=High resolution mass spectroscopy
LCMS=Liquid chromatography-mass spectroscopy
ESI-TOF=Electrosprayionization-time of flight
MW=Microwave
W=Watt
psi=Pounds per square inch The presently disclosed compounds exhibit broad anticancer activity against multiple cancer cell lines. Thereby, the compounds of formulas A and B disclosed herein can be used in medications for the prevention and/or treatment of a variety of cancers.

The compounds and medications described herein may be used in any type of mammalian subject, such as dogs, cats, cows, sheep, horses, and/or humans. The effective amounts of the disclosed compounds may vary according to the particulars of the disease being treated. Effective amounts of the disclosed compounds and medications will be readily ascertainable to those skilled in the art upon consideration of the subject disclosure.

The disclosed compounds can be formulated as pharmaceutical compositions and administered to a patient, such as a human patient, in a variety of forms adapted to the chosen route of administration, i.e., orally or parenterally, by intravenous, intra muscular, topical, and/or subcutaneous routes.

The disclosed compounds may be used in combination with one or more other anticancer agents, in some embodiments. Suitable anticancer agents include but are not limited to: alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, protein synthesis inhibitors, kinase inhibitors, antiestrogens, cisplatin, carboplatin, interferon, asparginase, leuprolide, flutamide, megestrol, mitomycin, bleomycin, doxorubicin, Adriamycin, and/or taxol.

The subject disclosure provides novel heterocyclic fused constrained ring systems of general formulas A and B, methods of preparing these systems, and the use of such novel compounds for many disease states, including as anticancer agents. The following experimental examples are provided for further clarification and explanation of the disclosed subject matter and are not intended to limit the scope of the present disclosure in any way.

Example 1

An example process for the preparation of novel compounds of the general formula A and characterization data for the selected compounds of this class are described in this experimental example.

Procedure i: Aldehyde (general formula I, 0.6 mmol) and 2-aminoazine (general formula II, 0.5 mmol) were mixed in acetonitrile (5 mL) at room temperature. Then, TFA (1.0 mmol) was added dropwise and refluxed for 24 hours. After completion of the reaction, acetonitrile and excess TFA was removed under vacuum and concentrated to dryness. The crude material was triturated using a mixture of EtOAc and diethyl ether in different ratios to yield pure compounds of general formula A.

Procedure ii: Aldehyde (General formula I, 0.6 mmol) and 2-aminoazine (General formula II, 0.5 mmol) were mixed in 1,4-dioxane (5 mL) at room temperature. Then, scandium triflate (20 mol %) was added and continued stirring at room temperature for 6 hours. Then, the reaction mixture was heated at 80° C. for 12-16 hours. After completion of the reaction, 1,4-dioxane was removed under vacuum and concentrated to dryness. The crude material was purified on flash chromatography using EtOAc/hexane or MeOH/DCM as mobile phase gradient to yield pure compounds of general formula A.

Compound 1a was prepared following the general reaction procedure i and had the following chemical structure and characterization data:

Compound 1a

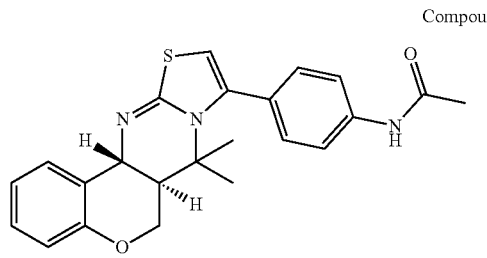

N-(4-((6aS,12aR)-7,7-dimethyl-6a,12a-dihydro-6H,7H-chromeno[4,3-d]thiazolo[3,2-a]pyrimidin-9-yl)phenyl)acetamide (Pale yellow solid, 105 mg, yield 52%); $^1$H NMR (400 MHz, CDCl$_3$) δ 7.83 (d, J=7.6 Hz, 1H), 7.63-7.53 (m, 2H), 7.36 (d, J=8.4 Hz, 2H), 7.14 (dd, J=11.2, 4.1 Hz, 1H), 7.04-6.97 (m, 1H), 6.80 (d, J=8.1 Hz, 1H), 5.60 (s, 1H), 4.52 (d, J=11.0 Hz, 1H), 4.28 (dd, J=10.7, 3.0 Hz, 1H), 3.91 (t, J=10.9 Hz, 1H), 2.20 (s, 3H), 1.89 (td, J=11.0, 3.0 Hz, 1H), 1.32 (s, 3H), 1.25 (s, 3H); $^{13}$C NMR (100 MHz, CDCl$_3$) δ 168.5, 163.2, 153.6, 139.6, 138.7, 131.3, 130.3, 128.5, 128.0, 125.4, 121.3, 119.1, 116.0, 100.6, 66.0, 60.6, 52.2, 42.8, 27.3, 25.0, 24.6; HRMS (ESI-TOF): m/z calcd for C$_{23}$H$_{24}$N$_3$O$_2$S 406.1589, found 406.1584 [M+H]$^+$.

Compound 1b was prepared following the general reaction procedure i and had the following chemical structure and characterization data:

Compound 1b

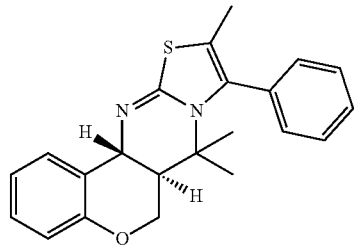

(6aS,12aR)-7,7,10-trimethyl-9-phenyl-6a,12a,dihydro-6H,7H,chromeno[4,3-d]thiazolo[3,2-a]pyrimidine (White solid, 106 mg, yield 59%); $^1$H NMR (400 MHz, CDCl$_3$) δ 7.86 (d, J=7.6 Hz, 1H), 7.48-7.41 (m, 3H), 7.41-7.32 (m, 2H), 7.19-7.12 (m, 1H), 7.03 (td, J=7.5, 1.0 Hz, 1H), 6.81 (dd, J=8.1, 0.9 Hz, 1H), 4.49 (d, J=11.0 Hz, 1H), 4.27 (dd, J=10.6, 3.1 Hz, 1H), 3.91 (t, J=10.9 Hz, 1H), 1.90 (td, J=11.0, 3.0 Hz, 1H), 1.74 (s, 3H), 1.27-1.22 (two s, 6H); $^{13}$C NMR (101 MHz, CDCl$_3$) δ 162.1, 153.6, 134.1, 133.7, 132.1, 131.4, 128.9, 128.6, 128.5, 128.2, 127.9, 121.3, 115.9, 66.1, 60.1, 52.0, 43.0, 27.3, 24.8, 12.5; HRMS (ESI-TOF): m/z calcd for C$_{22}$H$_{23}$N$_2$OS 363.1531, found 363.1539 [M+H]$^+$.

Compound 1c was prepared following the general reaction procedure i and had the following chemical structure and characterization data:

Compound 1c

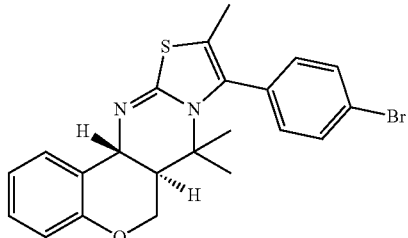

(6aS,12aR)-9-(4-bromophenyl)-7,7,10-trimethyl-6a,12a-dihydro-6H,7H-chromeno[4,3-d]thiazolo[3,2-a]pyrimidine (Pale yellow solid, 121 mg, yield 55%); $^1$H NMR (400 MHz, CDCl$_3$) δ 7.84 (d, J=7.6 Hz, 1H), 7.64-7.56 (m, 2H), 7.28-7.20 (m, 2H), 7.19-7.12 (m, 1H), 7.02 (td, J=7.6, 0.9 Hz, 1H), 6.85-6.77 (m, 1H), 4.46 (d, J=11.0 Hz, 1H), 4.27 (dd, J=10.6, 3.0 Hz, 1H), 3.92 (t, J=10.9 Hz, 1H), 1.88 (td, J=11.0, 2.9 Hz, 1H), 1.74 (s, 3H), 1.27-1.21 (two s, 6H); $^{13}$C NMR (125 MHz, CDCl$_3$) δ 162.3, 153.5, 133.6, 132.9, 132.0, 131.7, 128.5, 128.2, 123.5, 121.5, 116.1, 65.8, 60.8, 51.5, 43.0, 27.3, 24.9, 12.5; HRMS (ESI-TOF): m/z calcd for C$_{22}$H$_{22}$BrN$_2$OS 441.0636, found 441.0633 [M+H]$^+$.

Compound 1d was prepared following the general reaction procedure i and had the following chemical structure and characterization data:

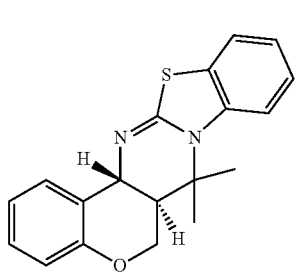

Compound 1d (6aS,14aR)-7,7-dimethyl-6a,14a-dihydro-6H,7H-benzo[4,5]thiazolo[3,2-a]chromeno[4,3-d]pyrimidine (White solid, 122 mg, yield 76%); $^1$H NMR (400 MHz, MeOH-d$_4$) δ 7.72-7.65 (m, 1H), 7.44-7.36 (m, 2H), 7.28-7.19 (m, 1H), 7.15-7.09 (m, 1H), 7.06 (td, J=7.7, 0.9 Hz, 1H), 6.95 (td, J=7.5, 1.2 Hz, 1H), 6.78 (dd, J=8.2, 1.1 Hz, 1H), 4.57 (d, J=11.0 Hz, 1H), 4.53 (dd, J=10.8, 3.0 Hz, 1H), 4.05 (t, J=11.0 Hz, 1H), 1.96 (td, J=11.0, 3.0 Hz, 1H), 1.81 (s, 3H), 1.60 (s, 3H); $^{13}$C NMR (101 MHz, MeOH-d$_4$) δ 162.2, 155.4, 140.2, 129.7, 129.2, 126.6, 126.1, 124.7, 123.4, 123.3, 121.9, 117.3, 114.9, 66.7, 60.6, 53.1, 45.6, 25.2, 22.0; HRMS (ESI-TOF): m/z calcd for C$_{19}$H$_{19}$N$_2$OS, 323.1218, found 323.1228 [M+H]$^+$.

Compound 1e was prepared following the general reaction procedure i and had the following chemical structure and characterization data:

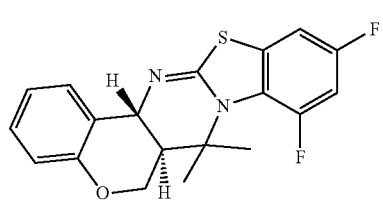

Compound 1e (6aS,14aR)-9,11-difluoro-7,7-dimethyl-6a,14a-dihydro-6H,7H-benzo[4,5]thiazolo[3,2-a]chromeno[4,3-d]pyrimidine (Pale yellow solid, 149 mg, yield 79%); $^1$H NMR (400 MHz, CDCl$_3$) δ 7.82 (d, J=7.7 Hz, 1H), 7.22-7.16 (m, 1H), 7.05 (td, J=7.6, 1.1 Hz, 1H), 6.94-6.92 (m, 1H), 6.85 (dd, J=8.2, 1.0 Hz, 1H), 6.81-6.73 (m, 1H), 4.54 (d, J=11.0 Hz, 1H), 4.47 (dd, J=10.7, 3.0 Hz, 1H), 4.08 (t, J=10.9 Hz, 1H), 1.97 (td, J=11.0, 3.0 Hz, 1H), 1.71 (d, J=2.0 Hz, 3H), 1.57 (s, 3H); $^{13}$C NMR (101 MHz, CDCl$_3$) δ 158.2, 157.7 (dd, 1C), 153.7, 146.0 (dd, 1C), 128.7-128.4 (m, 2C), 128.2, 124.8, 123.9 (dd, 1C), 121.4, 116.2, 105.6 (dd, 1C), 102.3 (dd, 1C), 65.9, 60.2, 51.7, 44.0 (d, 1C), 26.0 (d, 1C), 23.7 (d, 1C); HRMS (ESI-TOF): m/z calcd for C$_{19}$H$_{17}$F$_2$N$_2$OS 359.1029, found 359.1033 [M+H]$^+$.

Compound 1f was prepared following the general reaction procedure i and had the following chemical structure and characterization data:

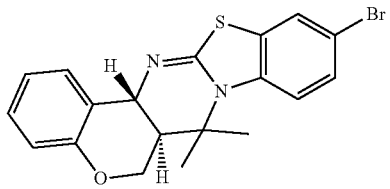

Compound 1f (6aS,14aR)-11-bromo-7,7-dimethyl-6a,14a-dihydro-6H,7H-benzo[4,5]thiazolo[3,2-a]chromeno[4,3-d]pyrimidine (White solid, 134 mg, yield 67%); $^1$H NMR (400 MHz, CDCl$_3$) δ 7.83 (d, J=7.7 Hz, 1H), 7.43 (d, J=2.1 Hz, 1H), 7.30-7.26 (m, 1H), 7.22-7.13 (m, 1H), 7.08-6.95 (m, 2H), 6.83 (dd, J=8.2, 0.8 Hz, 1H), 4.55 (d, J=11.1 Hz, 1H), 4.49 (dd, J=10.7, 3.0 Hz, 1H), 4.07 (t, J=10.9 Hz, 1H), 2.07 (td, J=11.1, 2.9 Hz, 1H), 1.79 (s, 3H), 1.55 (s, 3H); $^{13}$C NMR (101 MHz, CDCl$_3$) δ 158.4, 153.5, 138.2, 128.3, 128.2, 127.9, 126.2, 124.9, 124.7, 121.3, 116.1, 114.1, 113.5, 65.6, 58.7, 52.0, 43.4, 24.9, 21.8; HRMS (ESI-TOF): m/z calcd for C$_{19}$H$_{18}$BrN$_2$OS, 401.0318, found 402.0329 [M+H]$^+$.

Compound 1g was prepared following the general reaction procedure i and had the following chemical structure and characterization data:

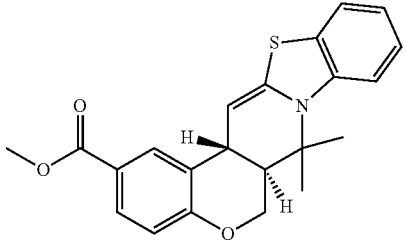

Compound 1g methyl (6aS, 14aR)-7,7-dimethyl-6a,14a-dihydro-6H,7H-benzo[4,5]thiazolo[3,2-a]chromeno[4,3-d]pyrimidine-2-carboxylate (White solid, 106 mg, yield 59%); $^1$H NMR (400 MHz, CDCl$_3$) δ 7.86 (d, J=7.6 Hz, 1H), 7.48-7.41 (m, 3H), 7.41-7.32 (m, 2H), 7.19-7.12 (m, 1H), 7.03 (td, J=7.5, 1.0 Hz, 1H), 6.81 (dd, J=8.1, 0.9 Hz, 1H), 4.49 (d, J=11.0 Hz, 1H), 4.27 (dd, J=10.6, 3.1 Hz, 1H), 3.91 (t, J=10.9 Hz, 1H), 1.90 (td, J=11.0, 3.0 Hz, 1H), 1.74 (s, 3H), 1.27-1.22 (two s, 6H); $^{13}$C NMR (101 MHz, CDCl$_3$) δ 162.1, 153.6, 134.1, 133.7, 132.1, 131.4, 128.9, 128.6, 128.5, 128.2, 127.9, 121.3, 115.9, 66.1, 60.1, 52.0, 43.0, 27.3, 24.8, 12.5; HRMS (ESI-TOF): m/z calcd for C$_{22}$H$_{23}$N$_2$OS 363.1531, found 363.1539 [M+H]$^+$.

Compound 1h was prepared following the general reaction procedure ii and had the following chemical structure and characterization data:

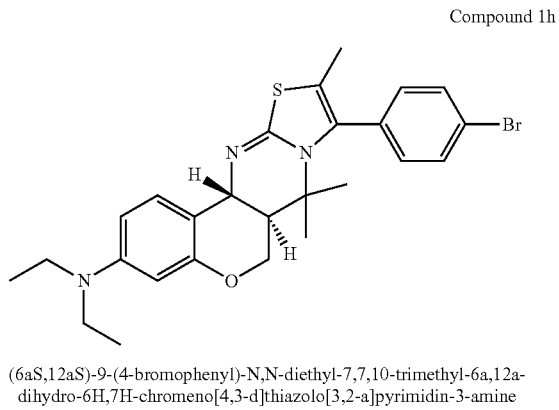 [SMILES: CCN(CC)c1ccc2c(c1)OC[C@H]1[C@H]2N=C2SC(C)=C(c3ccc(Br)cc3)N2C1(C)C]

Compound 1h (6aS,12aS)-9-(4-bromophenyl)-N,N-diethyl-7,7,10-trimethyl-6a,12a-dihydro-6H,7H-chromeno[4,3-d]thiazolo[3,2-a]pyrimidin-3-amine (Orange color solid, 97 mg, yield 38%); $^1$H NMR (500 MHz, CDCl$_3$) δ 7.66-7.63 (m, 2H), 7.60 (d, J=8.7 Hz, 1H), 7.28-7.24 (m, 2H), 6.45 (dd, J=8.7, 2.5 Hz, 1H), 6.11 (d, J=2.5 Hz, 1H), 4.58 (d, J=10.9 Hz, 1H), 4.24 (dd, J=10.7, 2.8 Hz, 1H), 3.87 (t, J=10.8 Hz, 1H), 3.33 (q, J=7.1 Hz, 2H), 2.05-1.99 (m, 1H), 1.81 (s, 3H), 1.31 (d, J=2.1 Hz, 6H), 1.15 (t, J=7.0 Hz, 6H). $^{13}$C NMR (126 MHz, CDCl$_3$) δ 163.1, 154.4, 148.5, 133.7, 133.6, 132.9, 132.3, 132.0, 131.2, 128.3, 124.1, 106.6, 98.5, 65.3, 62.4, 50.0, 44.4, 43.9, 27.1, 24.9, 12.5, 12.4. HRMS (ESI-TOF): m/z calcd for C$_{26}$H$_{31}$BrN$_3$OS 512.1371, found 512.1367 [M+H]$^+$.

Compound 1l was prepared following the general reaction procedure ii and had the following chemical structure and characterization data:

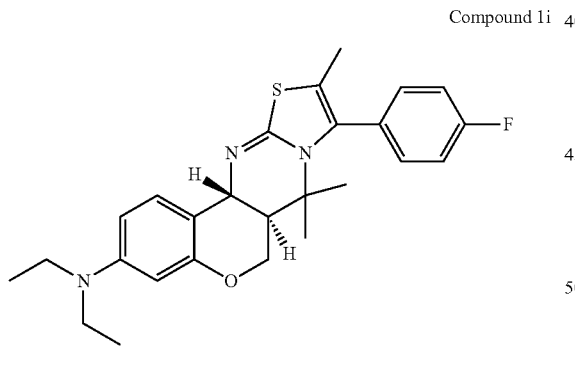

Compound 1i (6aS,12aS)-N,N-diethyl-9-(4-fluorophenyl)-7,7,10-trimethyl-6a,12a-dihydro-6H,7H-chromeno[4,3-d]thiazolo[3,2-a]pyrimidin-3-amine (Orange color solid, 78 mg, yield 36%); $^1$H NMR (500 MHz, CDCl$_3$) δ 7.63 (d, J=8.6 Hz, 1H), 7.40-7.32 (m, 2H), 7.22-7.13 (m, 2H), 6.51-6.38 (m, 1H), 6.09 (d, J=2 Hz, 1H), 4.49 (d, J=10.8 Hz, 1H), 4.23 (dd, J=10.5, 2.4 Hz, 1H), 3.88 (t, J=10.8 Hz, 1H), 3.33 (q, J=7.1 Hz, 2H), 1.96-1.88 (m, 1H), 1.76 (s, 3H), 1.28 (two s, 6H), 1.15 (t, J=6.9 Hz, 6H). $^{13}$C NMR (125 MHz, CDCl$_3$) δ 163.0 (d, J1C—F=250 Hz), 162.25, 154.5, 148.2, 134.0, 133.3, 132.9, 129.0, 128.7, 115.8, 115.6, 106.6, 98.6, 65.81, 61.11, 50.91, 44.48, 43.84, 27.25, 24.90, 12.57, 12.47. HRMS (ESI-TOF): m/z calcd for C$_{26}$H$_{31}$FN$_3$OS 452.2171, found 452.2169 [M+H]$^+$.

Compound 1j was prepared following the general reaction procedure i and had the following chemical structure and characterization data:

Compound 1j: (8aS,14aS)-9,9-dimethyl-11-phenyl-8a,14a-dihydro-8H,9H-benzo[5,6]chromeno[4,3-d]thiazolo[3,2-a]pyrimidine

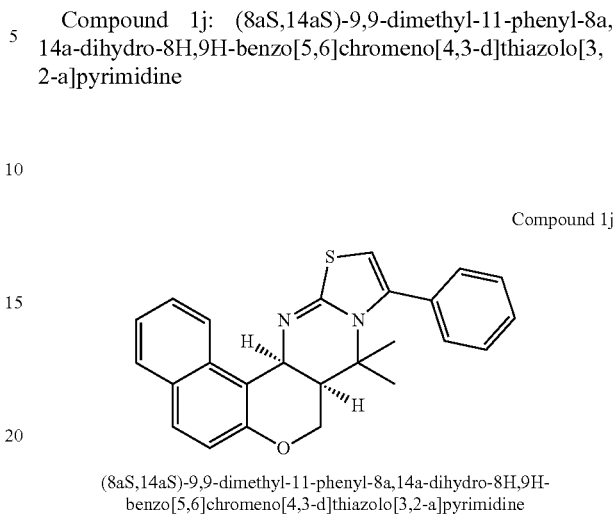

Compound 1j (8aS,14aS)-9,9-dimethyl-11-phenyl-8a,14a-dihydro-8H,9H-benzo[5,6]chromeno[4,3-d]thiazolo[3,2-a]pyrimidine (White solid, 103 mg, 52%); $^1$H NMR (400 MHz, Acetone) δ 7.92 (d, J=8.2 Hz, 1H), 7.54 (d, J=8.2 Hz, 2H), 7.47-7.18 (m, 6H), 7.09 (t, J=7.3 Hz, 1H), 6.78 (d, J=8.9 Hz, 1H), 6.40 (s, 1H), 5.31 (d, J=3.6 Hz, 2H), 4.29 (d, J=10.9 Hz, 1H), 3.75 (t, J=11.6 Hz, 1H), 2.34-2.24 (m, 1H), 1.68 (s, 3H), 1.03 (s, 3H). $^{13}$C NMR (100 MHz, Acetone) δ 163.7, 152.0, 140.4, 132.8, 132.2, 130.9, 130.2, 129.2, 128.6, 128.3 (2C), 127.2, 123.8, 122.5, 118.1, 110.5, 106.1, 61.6, 61.4, 43.9, 39.8, 30.0, 25.91. HRMS (ESI-TOF): m/z calcd for C$_{25}$H$_{23}$N$_2$OS 399.1531, found 399.1526 [M+H]$^+$.

Compound 1k was prepared following the general reaction procedure i and had the following chemical structure and characterization data:

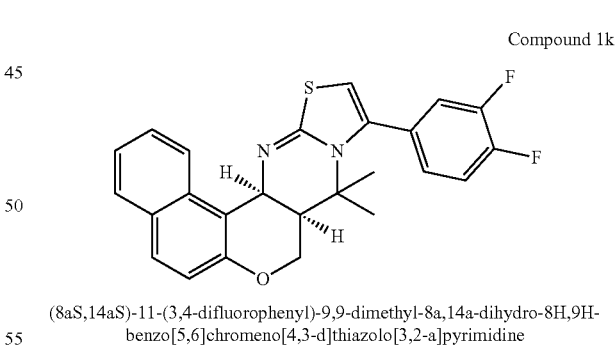

Compound 1k (8aS,14aS)-11-(3,4-difluorophenyl)-9,9-dimethyl-8a,14a-dihydro-8H,9H-benzo[5,6]chromeno[4,3-d]thiazolo[3,2-a]pyrimidine (White solid, 110 mg, 51%); $^1$H NMR (400 MHz, MeOD) δ 8.17 (d, J=8.5 Hz, 1H), 7.90 (dd, J=8.3, 5.9 Hz, 2H), 7.74-7.62 (m, 2H), 7.55-7.45 (m, 3H), 7.15 (d, J=9.0 Hz, 1H), 6.87 (s, 1H), 5.64 (d, J=3.2 Hz, 1H), 4.62 (dd, J=11.8, 2.7 Hz, 1H), 3.93 (t, J=11.8 Hz, 1H), 2.65 (dt, J=12.2, 3.6 Hz, 1H), 1.91 (s, 3H), 1.34 (s, 3H). $^{13}$C NMR (100 MHz, MeOD) δ 164.0, 152.9, 151.8, 151.7, 138.9, 132.2, 131.2, 129.5, 128.6, 128.2 (2C), 127.5, 123.9, 121.0, 118.1, 117.7 (2C), 109.2, 107.8, 62.5, 61.0, 43.4, 39.2, 29.3, 25.4. LCMS (ESI): m/z 435 [M+H]$^+$.

Compound 11 was prepared following the general reaction procedure i and had the following chemical structure and characterization data:

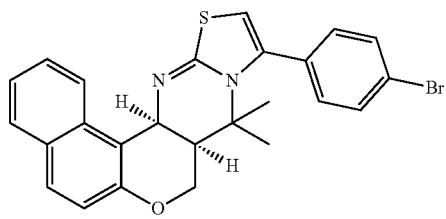

Compound 11

(8aS,14aS)-11-(4-bromophenyl)-9,9-dimethyl-8a,14a-dihydro-8H,9H-benzo[5,6]chromeno[4,3-d]thiazolo[3,2-a]pyrimidine (White solid, 130 mg, 55%); $^1$H NMR (400 MHz, Acetone) δ 8.21 (d, J=8.5 Hz, 1H), 7.94 (d, J=9.0 Hz, 2H), 7.82 (d, J=8.2 Hz, 2H), 7.77-7.58 (m, 3H), 7.47 (t, J=7.3 Hz, 1H), 7.16 (d, J=9.0 Hz, 1H), 6.99 (s, 1H), 5.79 (d, J=3.0 Hz, 1H), 4.69 (dd, J=11.4, 2.8 Hz, 1H), 4.12 (t, J=11.8 Hz, 1H), 2.80 (d, J=12.3 Hz, 1H), 2.08 (s, 3H), 1.47 (s, 3H). MR (100 MHz, Acetone) δ 164.2, 152.3, 139.9, 132.3, 132.0, 131.4, 130.8, 129.3, 128.8, 127.6, 124.5, 124.1, 121.7, 118.4, 117.8, 114.9, 109.6, 107.6, 62.8, 61.3, 43.7, 39.3, 30.1, 26.0. HRMS (ESI-TOF): m/z calcd for $C_{25}H_{22}BrN_2OS$ 477.0636, found 477.0636 [M+H]$^+$.

Compound 1m was prepared following the general reaction procedure i and had the following chemical structure and characterization data:

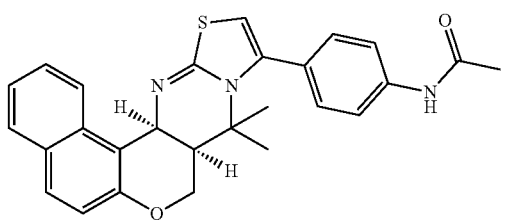

Compound 1m

N-(4-((8aS,14aS)-9,9-dimethyl-8a,14a-dihydro-8H,9H-benzo[5,6]chromeno[4,3-d]thiazolo[3,2-a]pyrimidin-11-yl)phenyl)acetamide (White solid, 134 mg, 59%); $^1$H NMR (400 MHz, MeOH-d$_4$) δ 8.17 (d, J=8.4 Hz, 1H), 7.95-7.85 (m, 2H), 7.78 (d, J=6.4 Hz, 2H), 7.74-7.64 (m, 1H), 7.50 (dd, J=17.6, 10.2 Hz, 3H), 7.15 (d, J=8.9 Hz, 1H), 6.77 (s, 1H), 5.63 (d, J=2.2 Hz, 1H), 4.61 (d, J=8.6 Hz, 1H), 3.93 (t, J=11.8 Hz, 1H), 2.63 (d, J=12.1 Hz, 1H), 2.20 (s, 3H), 1.91 (s, 3H), 1.31 (s, 3H); $^{13}$C NMR (101 MHz, MeOH-d$_4$) δ 170.6, 163.8, 152.1, 141.2, 140.9, 132.2, 131.2, 129.5, 128.6, 127.5, 126.1, 123.9, 121.0, 119.2, 118.1, 109.3, 106.5, 62.3, 61.0, 43.3, 39.3, 29.3, 25.3, 22.6; HRMS (ESI-TOF): m/z calcd for $C_{27}H_{26}N_3O_2S$ 456.1745, found 456.1750 [M+H]$^+$.

Compound 1n was prepared following the general reaction procedure i and had the following chemical structure and characterization data:

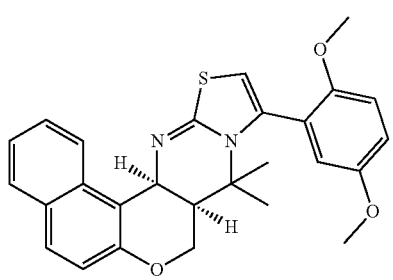

Compound 1n (8aS,14aS)-11-(2,5-dimethoxyphenyl)-9,9-dimethyl-8a,14a-dihydro-8H,9H-benzo[5,6]chromeno[4,3-d]thiazolo[3,2-a]pyrimidine (White solid, 82 mg, 36%); 1H NMR (400 MHz, CDCl$_3$) δ 8.24 (t, J=7.6 Hz, 1H), 7.82-7.73 (m, 2H), 7.68 (t, J=7.5 Hz, 1H), 7.43 (t, J=7.3 Hz, 1H), 7.09-7.01 (m, 2H), 6.97-6.83 (m, 2H), 6.23-6.11 (m, 1H), 5.40 (dd, J=3.3 Hz, 1H), 4.52-4.39 (m, 1H), 4.07-3.93 (m, 1H), 3.84 (two s, 6H), 2.31-2.21 (m, 1H), 1.73 (s, 3H), 1.29 (s, 3H). HRMS (ESI-TOF): m/z calcd for $C_{27}H_{27}N_2O_3S$ 459.1742, found 459.1736 [M+H]$^+$.

Compound 1o was prepared following the general reaction procedure i and had the following chemical structure and characterization data:

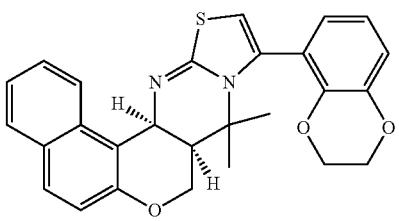

Compound 1o (8aS,14aS)-11-(2,3-dihydrobenzo[b][1,4]dioxin-5-yl)-9,9,12-trimethyl-8a,14a-dihydro-8H,9H-benzo[5,6]chromeno[4,3-d]thiazolo[3,2-a]pyrimidine (Off white solid, 79 mg, 35%); $^1$H NMR (500 MHz, MeOD) δ 8.17 (d, J=8.4 Hz, 1H), 7.90 (t, J=8.1 Hz, 2H), 7.69 (t, J=7.4 Hz, 1H), 7.49 (t, J=7.4 Hz, 1H), 7.19-6.98 (m, 4H), 6.73 (s, 1H), 5.62 (d, J=2.8 Hz, 1H), 4.65-4.58 (m, 2H), 4.41-4.30 (m, 4H), 3.91 (t, J=11.8 Hz, 1H), 2.67-2.59 (m, 1H), 1.91 (s, 3H), 1.33 (s, 3H). $^{13}$C NMR (125 MHz, MeOD) δ 165.1, 153.5, 147.22, 145.2, 142.5, 133.6, 132.6, 130.9, 130.0, 128.9, 125.3, 125.0, 124.7, 122.4, 121.7, 119.5, 118.5, 110.7, 107.8, 65.9, 65.7, 63.7, 62.4, 44.7, 40.7, 30.6, 26.5. LCMS (ESI): m/z 457 [M+H]$^+$.

Compound 1p was prepared following the general reaction procedure i and had the following chemical structure and characterization data:

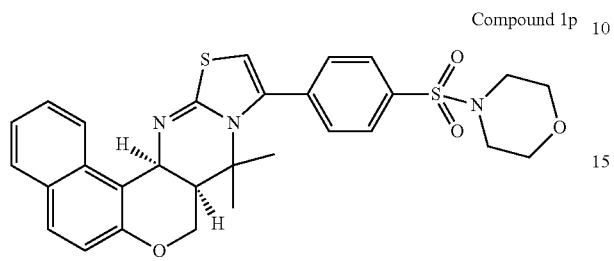

Compound 1p

8aS,14aS)-9,9-dimethyl-11-(4-(morpholinosulfonyl)phenyl)-8a,14a-dihydro-8H,9H-benzo[5,6]chromeno[4,3-d]thiazolo[3,2-a]pyrimidine (Off white solid, 114 mg, 42%); $^1$H NMR (500 MHz, MeOD) δ 8.18 (d, J=8.4 Hz, 1H), 8.02-7.86 (m, 6H), 7.74-7.67 (m, 1H), 7.53-7.47 (m, 1H), 7.16 (d, J=9.0 Hz, 1H), 6.93 (s, 1H), 5.66 (d, J=3.2 Hz, 1H), 4.62 (dd, J=11.3, 2.6 Hz, 1H), 3.95 (t, J=11.8 Hz, 1H), 3.79-3.72 (m, 4H), 3.09-3.01 (m, 4H), 2.67 (dt, J=12.3, 3.8 Hz, 1H), 1.95 (s, 3H), 1.29 (s, 3H). $^{13}$C NMR (126 MHz, MeOD) δ 165.6, 153.5, 140.7, 138.8, 137.5, 133.8, 133.5, 132.7, 130.9, 130.0, 129.4, 128.9, 125.3, 122.4, 119.5, 110.6, 109.1, 67.2, 64.0, 62.3, 47.5, 44.9, 40.5, 30.8, 26.9. LCMS (ESI): m/z 457 [M+H]$^+$.

Compound 1q was prepared following the general reaction procedure i and had the following chemical structure and characterization data:

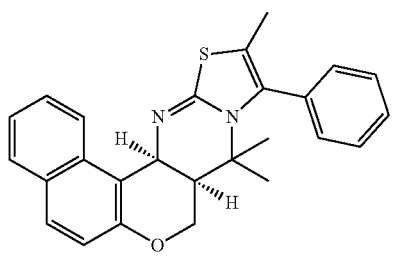

Compound 1q (8aS,14aS)-9,9,12-trimethyl-11-phenyl-8a,14a-dihydro-8H,9H-benzo[5,6]chromeno[4,3-d]thiazolo[3,2-a]pyrimidine (Off white solid, 113 mg, 55%); $^1$H NMR (400 MHz, CDCl$_3$) δ 8.15 (d, J=8.4 Hz, 1H), 7.77 (t, J=8.0 Hz, 2H), 7.69-7.63 (m, 1H), 7.61-7.52 (m, 3H), 7.46-7.37 (m, 2H), 7.35-7.30 (m, 1H), 7.04 (d, J=9.0 Hz, 1H), 5.43 (d, J=3.1 Hz, 1H), 4.47-4.40 (m, 1H), 3.99 (dd, J=11.9, 11.1 Hz, 1H), 2.27 (dt, J=12.1, 3.7 Hz, 1H), 1.88 (s, 3H), 1.79 (s, 3H), 1.14 (s, 3H). $^{13}$C NMR (100 MHz, CDCl$_3$) δ 162.3, 151.7, 134.7, 132.3, 131.8, 131.5, 130.61, 130.60, 130.5, 129.4, 129.3, 128.5, 127.9, 124.4, 121.7, 117.8, 109.3, 61.1, 60.9, 43.5, 40.9, 30.8, 26.8, 11.9. HRMS (ESI-TOF): m/z calcd for C$_{26}$H$_{25}$N$_2$OS 413.1687, found 413.1012 [M+H]$^+$.

Compound 1r was prepared following the general reaction procedure i and had the following chemical structure and characterization data:

Compound 1r (8aS,14aS)-11-(4-bromophenyl)-9,9,12-trimethyl-8a,14a-dihydro-8H,9H-benzo[5,6]chromeno[4,3-d]thiazolo[3,2-a]pyrimidine (White solid, 137 mg, 56%); $^1$H NMR (500 MHz, MeOD) δ 8.16 (d, J=8.4 Hz, 1H), 7.90 (t, J=8.2 Hz, 2H), 7.85-7.77 (m, 2H), 7.70 (dd, J=11.3, 4.1 Hz, 1H), 7.54 (dd, J=8.2, 2.1 Hz, 1H), 7.52-7.43 (m, 2H), 7.14 (d, J=9.0 Hz, 1H), 5.60 (d, J=3.1 Hz, 1H), 4.64-4.58 (m, 1H), 3.94 (t, J=11.8 Hz, 1H), 2.61 (dt, J=12.2, 3.8 Hz, 1H), 1.98 (s, 3H), 1.87 (s, 3H), 1.26 (s, 3H); $^{13}$C NMR (101 MHz, MeOD) δ 162.0, 152.1, 135.0, 133.9, 132.5, 132.4, 132.3, 132.2, 131.2, 129.5, 129.5, 128.6, 127.5, 124.8, 123.9, 121.0, 118.1, 117.9, 109.3, 62.2, 61.0, 43.1, 39.4, 29.2, 25.5, 10.5; HRMS (ESI-TOF): m/z calcd for C$_{26}$H$_{24}$BrN$_2$OS 491.0792, found 491.0784 [M+H]$^+$.

Compound 1s was prepared following the general reaction procedure i and had the following chemical structure and characterization data:

Compound 1s ethyl (8aS,14aS)-9,9-dimethyl-11-phenyl-8a,14a-dihydro-8H,9H-benzo[5,6]chromeno[4,3-d]thiazolo[3,2-a]pyrimidine-12-carboxylate (White solid, 119 mg, 51%); $^1$H NMR (400 MHz, MeOH-d$_4$) δ 8.17 (d, J=8.4 Hz, 1H), 7.91 (dd, J=8.3, 5.0 Hz, 2H), 7.75-7.56 (m, 6H), 7.50 (t, J=7.5 Hz, 1H), 7.15 (d, J=9.0 Hz, 1H), 5.64 (d, J=3.1 Hz, 1H), 4.63 (dd, J=11.3, 2.9 Hz, 1H), 4.04 (dt, J=23.6, 9.4 Hz, 3H), 2.66 (d, J=12.1 Hz, 1H), 1.90 (s, 3H), 1.22 (s, 3H), 0.99 (t, J=7.1 Hz, 3H); $^{13}$C NMR (101 MHz, MeOH-d$_4$) δ 163.3, 159.2, 152.2, 146.8, 132.1, 131.8, 131.4, 130.6, 129.7, 129.5, 128.7, 128.2, 127.6, 124.0, 120.9, 118.1, 113.3, 108.8, 63.8, 61.8, 60.9, 43.4, 39.5, 29.0, 25.5, 12.5; HRMS (ESI-TOF): m/z calcd for C$_{28}$H$_{27}$N$_2$O$_3$S 471.1742, found 471.1735 [M+H]$^+$.

Compound 1t was prepared following the general reaction procedure i and had the following chemical structure and characterization data:

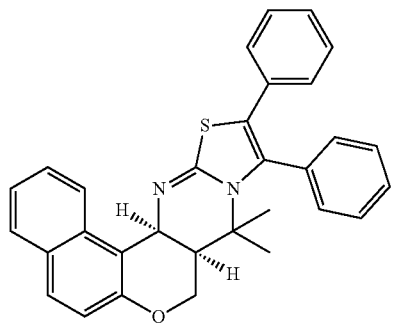

Compound 1t (8aS,14aS)-9,9-dimethyl-11,12-diphenyl-8a,14a-dihydro-8H,9H-benzo[5,6]chromeno[4,3-d]thiazolo[3,2-a]pyrimidine (White solid, 137 mg, 58%); $^1$H NMR (500 MHz, CDCl$_3$) δ 8.19 (d, J=8.4 Hz, 1H), 7.79 (t, J=7.6 Hz, 2H), 7.68 (t, J=7.5 Hz, 1H), 7.58-7.52 (m, 3H), 7.44 (dd, J=9.7, 5.4 Hz, 2H), 7.33 (d, J=7.6 Hz, 1H), 7.21 (dt, J=22.4, 7.2 Hz, 3H), 7.06 (d, J=9.0 Hz, 1H), 7.01 (d, J=7.2 Hz, 2H), 5.51 (d, J=3.1 Hz, 1H), 4.51 (dd, J=10.8, 2.2 Hz, 1H), 4.09 (t, J=11.5 Hz, 1H), 2.33 (dt, J=12.0, 3.5 Hz, 1H), 1.89 (s, 3H), 1.20 (s, 3H). $^{13}$C NMR (125 MHz, CDCl$_3$) δ 162.5, 151.8, 134.2, 132.5, 132.2, 131.7, 131.5, 130.8, 130.3, 129.3, 129.1, 128.9, 128.7, 128.6, 128.0, 124.5, 122.3, 121.7, 117.8, 117.7, 109.1, 61.55, 61.10, 43.62, 41.23, 30.81, 27.05. HRMS (ESI-TOF): m/z calcd for C$_{31}$H$_{27}$N$_2$OS 475.1844, found 475.1004 [M+H]$^+$.

Compound 1u was prepared following the general reaction procedure i and had the following chemical structure and characterization data:

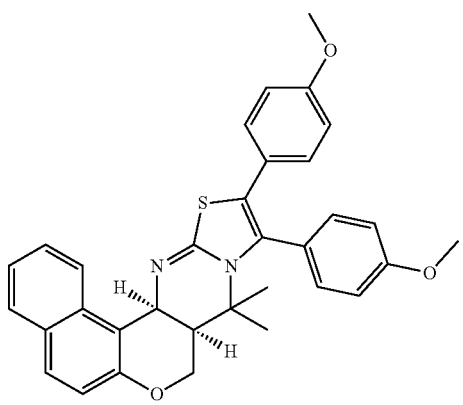

Compound 1u (8aS,14aS)-11,12-bis(4-methoxyphenyl)-9,9-dimethyl-8a,14a-dihydro-8H,9H-benzo[5,6]chromeno[4,3-d]thiazolo[3,2-a]pyrimidine (White solid, 128 mg, 48%). $^1$H NMR (500 MHz, MeOD) δ 8.25 (d, J=8.4 Hz, 1H), 7.81 (d, J=7.9 Hz, 1H), 7.73 (d, J=8.9 Hz, 1H), 7.61-7.55 (m, 1H), 7.51-7.47 (m, 1H), 7.41-7.36 (m, 1H), 7.26 (dd, J=8.5, 2.2 Hz, 1H), 7.08-7.04 (m, 2H), 7.00-6.92 (m, 3H), 6.72-6.67 (m, 2H), 5.32 (d, J=3.2 Hz, 1H), 4.50 (dd, J=10.6, 2.2 Hz, 1H), 4.03 (dd, J=12.0, 10.6 Hz, 1H), 3.86 (s, 3H), 3.71 (s, 3H), 2.16 (dt, J=12.0, 3.7 Hz, 1H), 1.72 (s, 3H), 1.10 (s, 3H). $^{13}$C NMR (125 MHz, MeOD) δ 160.8, 159.0, 158.9, 151.2, 134.0, 133.4, 133.1, 132.7, 129.5, 129.3, 129.1, 128.0, 126.3, 124.6, 123.1, 122.4, 117.9, 115.1, 114.0, 113.5, 113.3, 62.1, 58.1, 54.4, 54.2, 46.2, 41.2, 29.5, 26.4. LCMS (ESI): m/z 535 [M+H]$^+$.

Compound 1v was prepared following the general reaction procedure i and had the following chemical structure and characterization data:

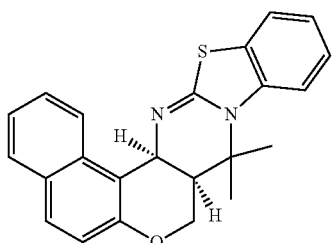

Compound 1v (8aS,16aS)-9,9-dimethyl-8a,16a-dihydro-8H,9H-benzo[4,5]thiazolo[3,2-a]benzo[5,6]chromeno[4,3-d]pyrimidine (Off white solid, 119 mg, 64%); $^1$H NMR (400 MHz, MeOH-d$_4$) δ 8.21 (d, J=8.5 Hz, 1H), 7.80 (d, J=8.1 Hz, 1H), 7.73 (d, J=9.0 Hz, 1H), 7.58-7.51 (m, 1H), 7.48 (d, J=8.3 Hz, 1H), 7.43-7.34 (m, 2H), 7.32-7.20 (m, 1H), 7.12-7.03 (m, 2H), 5.33 (d, J=2.5 Hz, 1H), 4.58-4.50 (m, 1H), 4.01 (dd, J=12.0, 10.8 Hz, 1H), 2.39 (dt, J=12.2, 3.6 Hz, 1H), 1.96 (s, 3H), 1.84 (s, 3H); $^{13}$C NMR (100 MHz, MeOH-d$_4$) δ 157.7, 151.4, 139.2, 133.0, 129.5, 129.2, 128.0, 126.4, 125.5, 123.1, 122.7, 122.2, 122.0, 121.8, 117.9, 115.4, 112.6, 62.1, 56.9, 46.6, 41.3, 26.8, 24.4; HRMS (ESI-TOF): m/z calcd for C$_{23}$H$_{21}$N$_2$OS 373.1374, found 373.1371 [M+H]*.

Compound 1w was prepared following the general reaction procedure i and had the following chemical structure and characterization data:

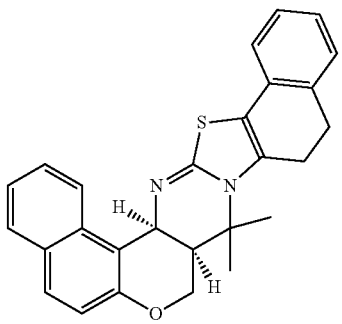

Compound 1w (8aS,18aS)-9,9-dimethyl-8a,11,12,18a-tetrahydro-8H,9H-benzo[5,6]chromeno[4,3-d]naphtho[2',1':4,5]thiazolo[3,2-a]pyrimidine (White solid, 101 mg, 48%). $^1$H NMR (400 MHz, MeOD) δ 8.20 (d, J=8.4 Hz, 1H), 7.95-7.86 (m, 3H), 7.70 (t, J=7.6 Hz, 1H), 7.55-7.33 (m, 4H), 7.16 (d, J=9.0 Hz, 1H), 5.74 (d, J=3.0 Hz, 1H), 4.60 (dd, J=11.8, 2.8 Hz, 1H), 3.73 (t, J=11.8 Hz, 1H), 3.02-2.78 (m, 4H), 2.46 (td, J=15.8, 5.6 Hz, 1H), 2.34 (s, 3H), 1.88 (s, 3H). $^{13}$C NMR (100 MHz, MeOD) δ 164.1, 152.0, 136.9, 136.7, 132.2, 131.3, 129.5, 128.6, 128.3, 128.3, 127.8, 127.6, 126.2, 125.0, 124.0, 123.2, 121.0, 118.1, 109.5, 63.5, 60.7, 43.6, 40.3, 29.1, 28.8, 24.9, 22.7. LCMS (ESI): m/z 425 [M+H]⁺.

Compound 1x was prepared following the general reaction procedure ii and had the following chemical structure and characterization data:

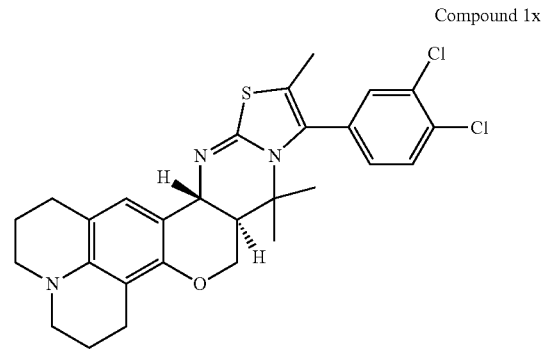

Compound 1x (5aS,11aR)-8-(3,4-dichlorophenyl)-6,6,9-trimethyl-2,3,5a,11a,14,15-hexahydro-1H,5H,6H,13H-pyrido[3,2,1-ij]thiazolo[3″,2″:1′,2′]pyrimido[4′,5′:4,5]pyrano[2,3-f]quinolone (Off white solid, 63 mg, 23%); ¹H NMR (500 MHz, CDCl₃) δ 7.59-7.53 (m, 1H), 7.40-7.37 (m, 2H), 7.33-7.25 (m, 1H), 4.52 (d, J=11.0 Hz, 1H), 4.31 (dd, J=10.6, 2.7 Hz, 1H), 3.82 (t, J=10.8 Hz, 1H), 3.12-3.04 (m, 4H), 2.88-2.80 (m, 1H), 2.79-2.70 (m, 1H), 2.68-2.61 (m, 1H), 2.59-2.51 (m, 1H), 2.03-1.89 (m, 5H), 1.77 (s, 3H), 1.29 (s, 3H), 1.27 (s, 3H). ¹³C NMR (125 MHz, CDCl₃) δ 162.1, 149.4, 143.0, 136.8, 136.4, 133.9, 130.4, 130.3 (2C), 129.5, 127.3, 124.9, 114.1, 115.6, 110.1, 108.4, 65.7, 61.1, 51.0, 50.2, 49.6, 43.3, 27.1, 25.2, 25.1, 22.4, 21.7, 21.1, 12.1. LCMS (ESI): m/z 526 [M+H]⁺.

Compound 1y was prepared following the general reaction procedure i and had the following chemical structure and characterization data:

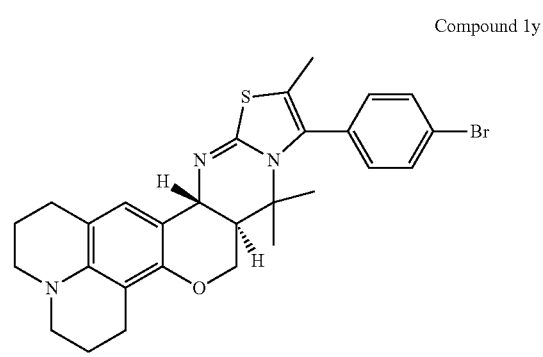

Compound 1y (5aS,11aR)-8-(4-bromophenyl)-6,6,9-trimethyl-2,3,5a,11a,14,15-hexahydro-1H,5H,6H,13H-pyrido[3,2,1-ij]thiazolo[3″,2″:1′,2′]pyrano[4′,5′:4,5]pyrano[2,3-f]quinolone (Off white solid, 67 mg, 25%); ¹H NMR (500 MHz, CDCl₃) δ 7.61 (t, J=7.2 Hz, 2H), 7.32 (s, 1H), 7.28-7.21 (m, 2H), 4.47 (d, J=10.8 Hz, 1H), 4.26 (dd, J=10.6, 2.8 Hz, 1H), 3.82 (t, J=10.8 Hz, 1H), 3.13-3.02 (m, 4H), 2.89-2.81 (m, 1H), 2.80-2.71 (m, 1H), 2.69-2.60 (m, 1H), 2.60-2.50 (m, 1H), 2.01-1.85 (m, 5H), 1.77 (s, 3H), 1.28 (s, 3H), 1.24 (s, 3H). ¹³C NMR (1265 MHz, CDCl₃) δ 162.3, 149.6, 143.1, 133.8, 133.2, 133.1, 132.1, 131.8, 125.4, 123.7, 115.8, 115.1, 108.5, 65.8, 61.5, 51.3, 50.4, 49.7, 43.9, 27.4, 27.3, 25.0, 22.6, 21.9, 21.2, 12.6. LCMS (ESI): m/z 536 [M+H]⁺.

Compound 1z was prepared following the general reaction procedure ii and had the following chemical structure and characterization data:

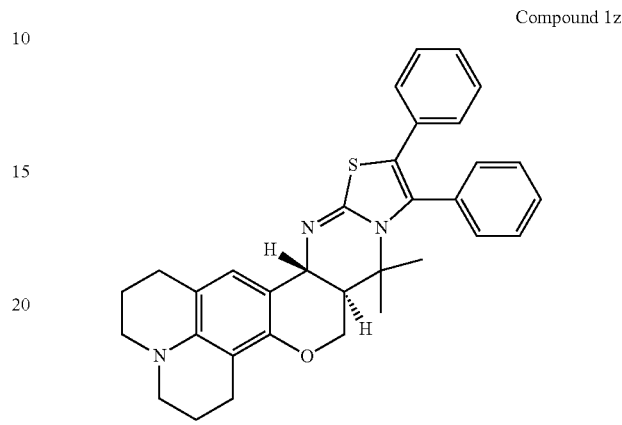

Compound 1z (5aS,11aR)-6,6-dimethyl-8,9-diphenyl-2,3,5a,11a,14,15-hexahydro-1H,5H,6H,13H-pyrido[3,2,1-ij]thiazolo[3″,2″:1′,2′]pyrimido[4′,5′:4,5]pyrano[2,3-f]quinolone (Off white solid, 72 mg, 28%); ¹H NMR (500 MHz, CDCl₃) δ 7.54 (d, J=7.2 Hz, 1H), 7.48-7.38 (m, 2H), 7.34-7.29 (m, 3H), 7.14-7.06 (m, 3H), 6.95-6.87 (m, 2H), 4.29 (dd, J=10.5, 2.6 Hz, 1H), 3.85 (t, J=10.8 Hz, 1H), 3.13-3.04 (m, 4H), 2.90-2.83 (m, 1H), 2.82-2.73 (m, 1H), 2.71-2.63 (m, 1H), 2.62-2.53 (m, 1H), 2.03-1.87 (m, 5H), 1.30 (s, 6H). ¹³C NMR (126 MHz, CDCl₃) δ 160.7, 149.6, 142.8, 134.6, 133.5, 132.8, 132.2, 129.2, 128.6, 128.5, 128.1, 126.9, 125.4, 122.9, 115.5, 113.3, 108.4, 66.1, 60.8, 51.9, 50.3, 49.7, 43.9, 27.5, 27.2, 24.8, 22.5, 21.9, 21.2. LCMS (ESI): m/z 520 [M+H]⁺.

Example 2

In a second experimental example, processes for the preparation of novel compounds of general formula B and characterization data for the selected compounds are disclosed.

Procedure iii: Aldehyde (general formula III, 0.6 mmol) and 2-aminoazine (general formula IV, 0.5 mmol) were mixed in a polar aprotic solvent (5 mL) at room temperature. Then, TFA (1.0 mmol) was added dropwise and refluxed for 24 hours. After completion of the reaction, solvent and excess reagent was removed under vacuum and concentrated to dryness. The crude material was triturated using a mixture of EtOAc and diethyl ether in different ratios to yield pure compounds of general formula B.

Procedure iv: Aldehyde (General formula III, 0.6 mmol) and desired 2-aminoazine (General formula H, 0.5 mmol) were mixed in a polar aprotic solvent (2 mL) at room temperature. Then, TFA (1.2 mmol) was added dropwise and the reaction mixture was carried out using MW (power 200 W, pressure 200 psi) at 110 to 150° C. for 20 mins. After completion of the reaction, solvent and excess reagent was removed under vacuum and concentrated to dryness. The crude material was purified by flash chromatography (DCM: EtOAc) using neutral alumina as a stationary phase to yield pure compounds of general formula B.

Compound 2a was prepared following the general reaction procedure ill and its chemical structure and characterization data is as follows:

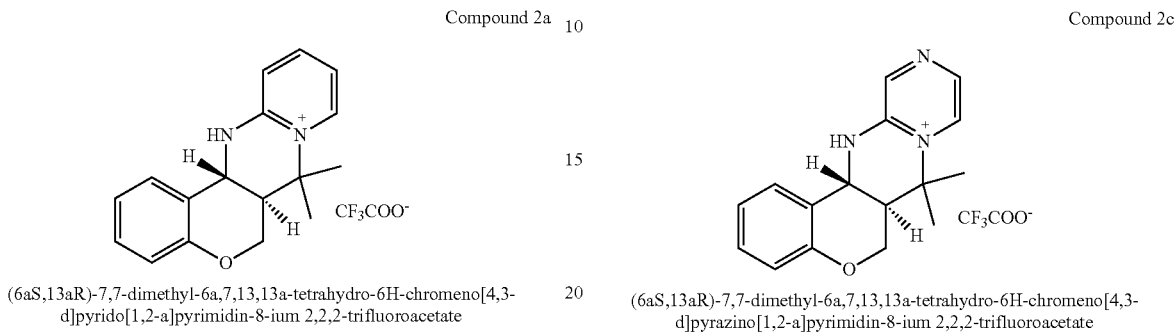

Compound 2a (6aS,13aR)-7,7-dimethyl-6a,7,13,13a-tetrahydro-6H-chromeno[4,3-d]pyrido[1,2-a]pyrimidin-8-ium 2,2,2-trifluoroacetate (White solid, 99 mg, yield 52%); $^1$H NMR (400 MHz, MeOH-d$_4$) δ 8.38 (d, J=7.1 Hz, 1H), 7.87-7.79 (m, 1H), 7.69 (d, J=7.6 Hz, 1H), 7.37-7.26 (m, 2H), 7.08 (td, J=7.7, 1.2 Hz, 1H), 7.01 (td, J=7.0, 1.3 Hz, 1H), 6.93 (d, J=8.2 Hz, 1H), 4.99 (d, J=11.3 Hz, 1H), 4.66 (dd, J=11.1, 3.0 Hz, 1H), 4.11 (t, J=11.1 Hz, 1H), 2.53 (td, J=11.2, 2.9 Hz, 1H), 1.94 (s, 3H), 1.67 (s, 3H); $^{13}$C NMR (101 MHz, MeOH-d$_4$) δ 153.6, 152.5, 140.7, 135.0, 129.3, 125.9, 120.9, 119.2, 116.8, 115.9, 113.8, 64.6, 64.6, 45.6, 41.2, 25.3, 23.6; HRMS (ESI-TOF): m/z calcd for $C_{17}H_{19}N_2O$ 267.1497, found $C_{17}H_{19}N_2O$ 267.1482 [M]$^+$.

Compound 2b was prepared following the general reaction procedure 1K and had the following chemical structure and characterization data:

Compound 2b (6aS,13aR)-7,7-dimethyl-6a,7,13,13a-tetrahydro-6H-chromeno[4,3-d]pyrimido[1,2-a]pyrimidin-8-ium 2,2,2-trifluoroacetate (White solid, 93 mg, yield 49%); $^1$H NMR (400 MHz, MeOH-d$_4$) δ 8.62 (dd, J=3.8, 1.9 Hz, 1H), 8.57 (dd, J=7.0, 1.8 Hz, 1H), 7.72 (d, J=7.8 Hz, 1H), 7.25 (t, J=7.5 Hz, 1H), 7.04 (t, J=7.5 Hz, 1H), 6.89 (d, J=8.2 Hz, 1H), 6.81 (dd, J=6.9, 4.0 Hz, 1H), 4.91 (d, J=11.2 Hz, 1H), 4.60 (dd, J=11.0, 3.0 Hz, 1H), 4.09 (t, J=11.0 Hz, 1H), 2.37 (td, J=11.1, 3.0 Hz, 1H), 1.84 (s, 3H), 1.60 (s, 3H); $^{13}$C NMR (101 MHz, MeOH-d$_4$) δ 163.7, 153.7, 153.3, 144.4, 128.8, 126.6, 120.8, 116.5, 108.3, 64.8, 64.2, 47.0, 40.9, 24.9, 23.2; HRMS (ESI-TOF): m/z calcd for $C_{16}H_{18}N_3O$ 268.1449, found 268.1447 [M]$^+$.

Compound 2c was prepared following the general reaction procedure 1K and had the following chemical structure and characterization data:

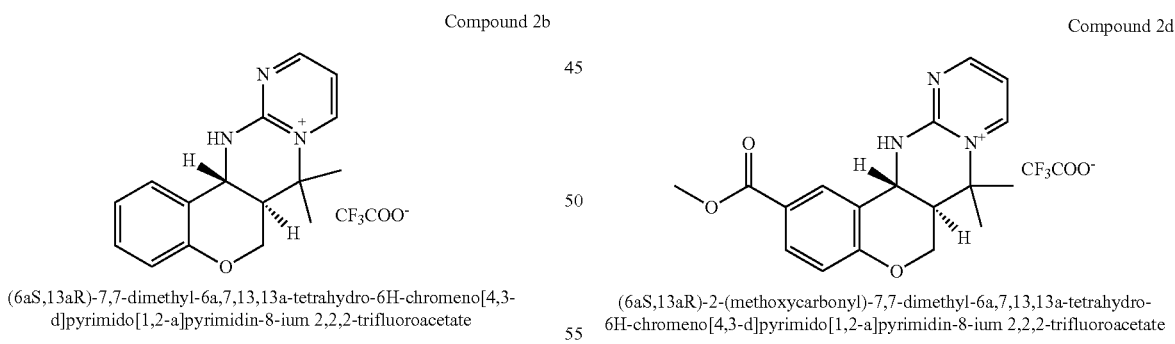

Compound 2c (6aS,13aR)-7,7-dimethyl-6a,7,13,13a-tetrahydro-6H-chromeno[4,3-d]pyrazino[1,2-a]pyrimidin-8-ium 2,2,2-trifluoroacetate (Off white solid, 142 mg, yield 75%); $^1$H NMR (400 MHz, MeOH-d$_4$) δ 7.89 (s, 1H), 7.77 (d, J=7.7 Hz, 1H), 7.34 (d, J=5.0 Hz, 1H), 7.15 (d, J=0.6 Hz, 1H), 6.99 (dd, J=7.5, 1.0 Hz, 1H), 6.87 (d, J=5.0 Hz, 1H), 6.80 (dd, J=8.2, 0.9 Hz, 1H), 4.54-4.48 (m, 2H), 4.01 (t, J=11.0 Hz, 1H), 1.88 (td, J=11.2, 3.1 Hz, 1H), 1.66 (s, 3H), 1.44 (s, 3H); $^{13}$C NMR (101 MHz, MeOH-d$_4$) δ 154.0, 151.1, 147.1, 127.7, 127.6, 124.8, 124.4, 120.5, 120.2, 115.9, 65.5, 59.0, 49.6, 40.6, 25.1, 23.3; HRMS (ESI-TOF): m/z calcd for $C_{16}H_{18}N_3O$ 268.1449, found 268.1422 [M]$^+$.

Compound 2d was prepared following the general reaction procedure 1K and had the following chemical structure and characterization data:

Compound 2d (6aS,13aR)-2-(methoxycarbonyl)-7,7-dimethyl-6a,7,13,13a-tetrahydro-6H-chromeno[4,3-d]pyrimido[1,2-a]pyrimidin-8-ium 2,2,2-trifluoroacetate (Off white solid, 133 mg, 70%); $^1$H NMR (400 MHz, MeOH-d$_4$) δ 8.84 (d, J=5.1 Hz, 2H), 8.46 (s, 1H), 7.96 (d, J=8.6 Hz, 1H), 7.19-7.12 (m, 1H), 7.03 (d, J=8.6 Hz, 1H), 5.10 (d, J=11.3 Hz, 1H), 4.74 (dd, J=11.1, 3.2 Hz, 1H), 4.23 (t, J=11.2 Hz, 1H), 3.93 (s, 3H), 2.63 (td, J=11.2, 3.1 Hz, 1H), 1.93 (s, 3H), 1.66 (s, 3H); $^{13}$C NMR (101 MHz, MeOH-d$_4$) δ 166.5, 165.0, 157.6, 154.0, 144.9, 130.9, 128.3, 123.1, 119.5, 117.0, 111.4, 65.5, 65.1, 51.1, 46.1, 40.3, 24.3, 23.2; HRMS (ESI-TOF): m/z calcd for $C_{18}H_{20}N_3O_3$ 326.1504, found 326.1565 [M]$^+$.

Compound 2e was prepared following the general reaction procedure 1K and had the following chemical structure and characterization data:

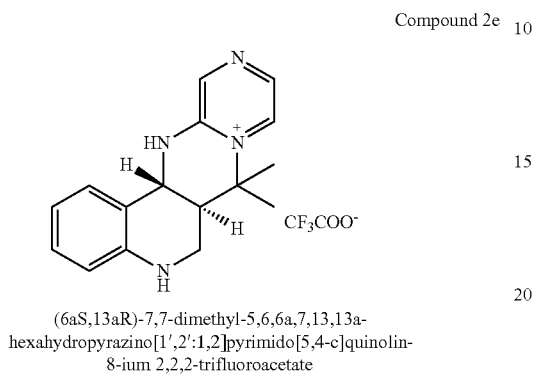

Compound 2e (6aS,13aR)-7,7-dimethyl-5,6,6a,7,13,13a-hexahydropyrazino[1',2':1,2]pyrimido[5,4-c]quinolin-8-ium 2,2,2-trifluoroacetate pale yellow solid (70 mg, 37%); $^1$H NMR (400 MHz, MeOH-$d_4$) δ 8.72 (s, 1H), 8.20 (d, J=4.5 Hz, 1H), 7.96 (d, J=4.7 Hz, 1H), 7.49 (d, J=7.8 Hz, 1H), 7.12 (t, J=7.6 Hz, 1H), 6.78 (t, J=7.4 Hz, 1H), 6.69 (d, J=8.1 Hz, 1H), 4.93 (d, J=11.1 Hz, 1H), 3.60 (dd, J=11.7, 3.2 Hz, 1H), 3.24 (t, J=11.4 Hz, 1H), 2.35 (td, J=11.2, 3.2 Hz, 1H), 1.89 (s, 3H), 1.64 (s, 3H); $^{13}$C NMR (101 MHz, MeOH-$d_4$) δ 146.7, 144.4, 143.3, 130.6, 128.7, 125.2, 125.0, 117.0, 116.3, 114.8, 65.7, 40.6, 40.3, 24.4, 23.1, 22.8; HRMS (ESI-TOF): m/z calcd for $C_{16}H_{19}N_4$, 267.1609, found 267.1619 [M]$^+$.

Compound 2f was prepared following the general reaction procedure 1K and had the following chemical structure and characterization data:

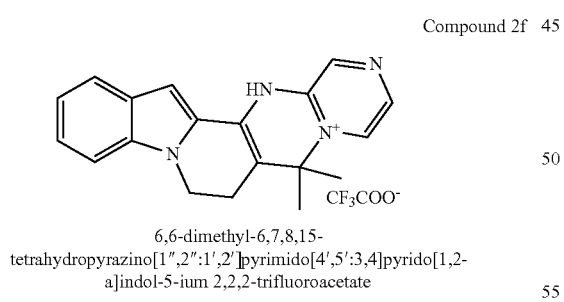

Compound 2f 6,6-dimethyl-6,7,8,15-tetrahydropyrazino[1",2":1',2']pyrimido[4',5':3,4]pyrido[1,2-a]indol-5-ium 2,2,2-trifluoroacetate (Brown solid, 116 mg, 56%); $^1$H NMR (400 MHz, MeOH-$d_4$) δ 8.69 (s, 1H), 8.21 (d, J=4.6 Hz, 1H), 8.12 (d, J=4.6 Hz, 1H), 7.48 (d, J=8.0 Hz, 1H), 7.30 (d, J=8.3 Hz, 1H), 7.18-7.09 (m, 1H), 6.97 (dd, J=11.1, 3.9 Hz, 1H), 6.83 (s, 1H), 4.11 (t, J=6.7 Hz, 2H), 2.71 (t, J=6.7 Hz, 2H), 1.89 (d, J=5.1 Hz, 6H); $^{13}$C NMR (101 MHz, MeOH-$d_4$) δ 142.7, 142.3, 137.3, 135.0, 128.2, 127.3, 125.3, 123.1, 120.9, 120.1, 119.8, 110.7, 109.0, 98.2, 67.2, 39.5, 26.3, 23.7; HRMS (ESI-TOF): m/z calcd for $C_{19}H_{19}N_4$, 303.1609, found 303.1596 [M]$^+$.

Compound 2g was prepared following the general reaction procedure iii and had the following chemical structure and characterization data:

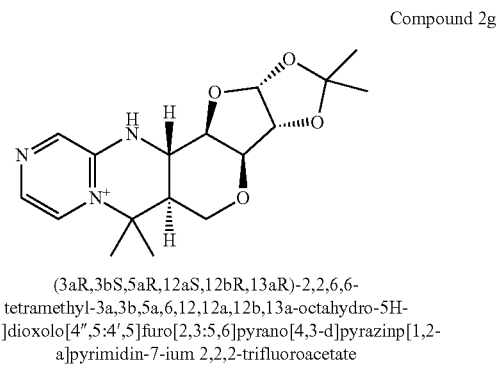

Compound 2g (3aR,3bS,5aR,12aS,12bR,13aR)-2,2,6,6-tetramethyl-3a,3b,5a,6,12,12a,12b,13a-octahydro-5H-[1,3]dioxolo[4",5':4',5]furo[2,3:5,6]pyrano[4,3-d]pyrazinp[1,2-a]pyrimidin-7-ium 2,2,2-trifluoroacetate (Brown solid, 82 mg, 37%); $^1$H NMR (400 MHz, MeOH-$d_4$) δ 8.44 (s, 1H), 8.06 (d, J=4.7 Hz, 1H), 7.86 (d, J=4.7 Hz, 1H), 5.94 (d, J=3.5 Hz, 1H), 4.68-4.50 (m, 2H), 4.24-4.00 (m, 3H), 3.47 (t, J=11.0 Hz, 1H), 2.35 (td, J=11.0, 3.2 Hz, 1H), 1.78 (s, 3H), 1.49 (two s, 6H), 1.32 (s, 3H); $^{13}$C NMR (101 MHz, MeOH-$d_4$) δ 146.1, 142.7, 130.3, 124.3, 112.0, 105.8, 83.2, 79.2, 73.5, 65.0, 63.4, 36.1, 25.5, 24.9, 23.5, 23.3, 22.8; HRMS (ESI-TOF): m/z calcd for $C_{17}H_{24}N_3O_4$, 334.1766, found 334.1777 [M]$^+$.

Compound 2h was prepared following the general reaction procedure iii and had the following chemical structure and characterization data:

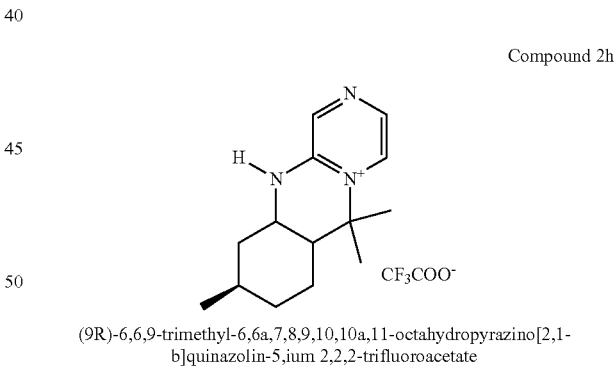

Compound 2h (9R)-6,6,9-trimethyl-6,6a,7,8,9,10,10a,11-octahydropyrazino[2,1-b]quinazolin-5,ium 2,2,2-trifluoroacetate (Brown solid, 105 mg, 60%); $^1$H NMR (400 MHz, MeOH-$d_4$) δ 7.81 (d, J=0.8 Hz, 1H), 7.75 (d, J=0.8 Hz, 0.6H), 7.32 (dd, J=5.0, 0.8 Hz, 0.6H), 7.24 (dd, J=4.9, 0.9 Hz, 1H), 6.89-6.84 (m, 1.6H), 3.92-3.86 (m, 1H), 3.18-3.10 (m, 0.6H), 2.26-2.19 (m, 0.6H), 2.13-2.03 (m, 1H), 1.97-1.90 (m, 1H), 1.89-1.81 (m, 0.6H), 1.77-1.68 (m, 2H), 1.68-1.57 (m, 2H), 1.55 (d, J=1.5 Hz, 6H), 1.43 (s, 3H), 1.38-1.15 (m, 5H), 1.07-0.88 (m, 8H); $^{13}$C NMR (101 MHz, MeOH-$d_4$) δ 149.9, 149.3, 145.9, 145.4, 124.4, 124.3, 120.6, 120.4, 60.1, 59.0, 52.2, 48.8, 44.3, 43.2, 40.3, 39.7, 34.3, 33.6, 31.5, 29.5, 26.0, 25.7, 23.8, 23.7, 23.0, 22.1, 21.1, 21.1; HRMS (ESI-TOF): m/z calcd for $C_{14}H_{22}N_3$, 232.1813, found 232.1813 [M]$^+$.

Compound 2i was prepared following the general reaction procedure iv and had the following chemical structure and characterization data:

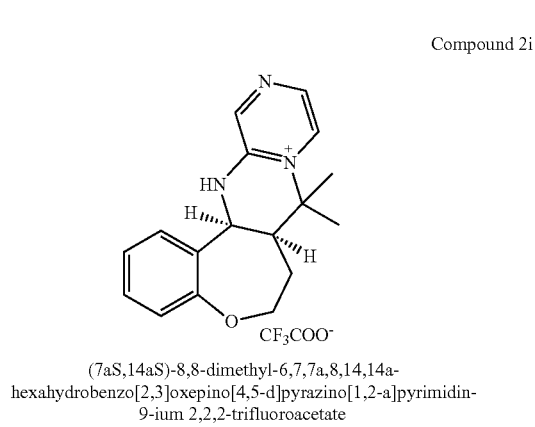

Compound 2i (7aS,14aS)-8,8-dimethyl-6,7,7a,8,14,14a-hexahydrobenzo[2,3]oxepino[4,5-d]pyrazino[1,2-a]pyrimidin-9-ium 2,2,2-trifluoroacetate (Off white solid, 160 mg, yield 81%); $^1$H NMR (400 MHz, MeOH-$d_4$) δ 8.45 (s, 1H), 8.08 (d, J=4.6 Hz, 1H), 7.95 (d, J=4.7 Hz, 1H), 7.54 (dd, J=7.5, 1.2 Hz, 1H), 7.42 (td, J=7.9, 1.5 Hz, 1H), 7.19 (td, J=7.5, 0.9 Hz, 1H), 7.10 (d, J=8.0 Hz, 1H), 5.22 (d, J=2.8 Hz, 1H), 4.46 (dt, J=12.5, 3.7 Hz, 1H), 3.82 (t, J=11.7 Hz, 1H), 2.60-2.50 (m, 1H), 2.24-2.14 (m, 1H), 1.94-1.80 (m, 7H); $^{13}$C NMR (101 MHz, MeOH-$d_4$) δ 160.8, 146.0, 142.3, 132.8, 131.0, 130.6, 126.7, 125.1, 123.7, 121.6, 71.4, 66.1, 55.2, 38.9, 30.2, 27.8, 24.3; HRMS (ESI-TOF): m/z calcd for $C_{17}H_{20}N_3O$, 282.1606, found 282.1632 [M]$^+$.

Compound 2j was prepared following the general reaction procedure iv and had the following chemical structure and characterization data:

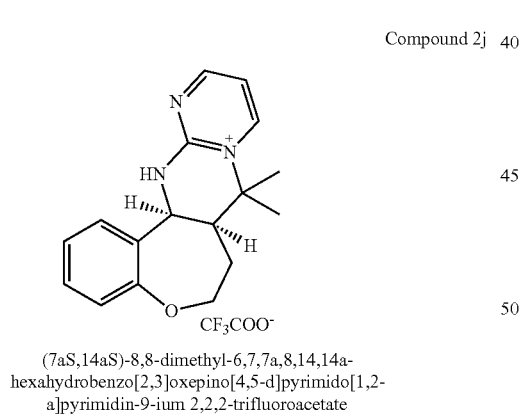

Compound 2j (7aS,14aS)-8,8-dimethyl-6,7,7a,8,14,14a-hexahydrobenzo[2,3]oxepino[4,5-d]pyrimido[1,2-a]pyrimidin-9-ium 2,2,2-trifluoroacetate (Pale yellow solid, 156 mg, yield 80%); $^1$H NMR (400 MHz, MeOH-$d_4$) δ 8.76 (dd, J=4.2, 1.9 Hz, 1H), 8.66 (dd, J=6.9, 1.9 Hz, 1H), 7.51 (dd, J=7.6, 1.5 Hz, 1H), 7.39 (td, J=7.9, 1.7 Hz, 1H), 7.17 (td, J=7.5, 1.2 Hz, 1H), 7.11-7.02 (m, 2H), 5.25 (d, J=3.3 Hz, 1H), 4.48-4.40 (m, 1H), 3.94-3.81 (m, 1H), 2.58-2.49 (m, 1H), 2.25-2.15 (m, 1H), 1.97-1.78 (m, 7H); $^{13}$C NMR (101 MHz, MeOH-$d_4$) δ 165.0, 160.3, 153.2, 145.0, 132.4, 130.7, 127.0, 123.6, 121.4, 110.8, 71.1, 66.8, 55.0, 39.6, 29.5, 27.6, 24.2; HRMS (ESI-TOF): m/z calcd for $C_{17}H_{20}N_3O$, 282.1606, found 282.1628 [M]$^+$.

Compound 2k was prepared following the general reaction procedure iv and had the following chemical structure and characterization data:

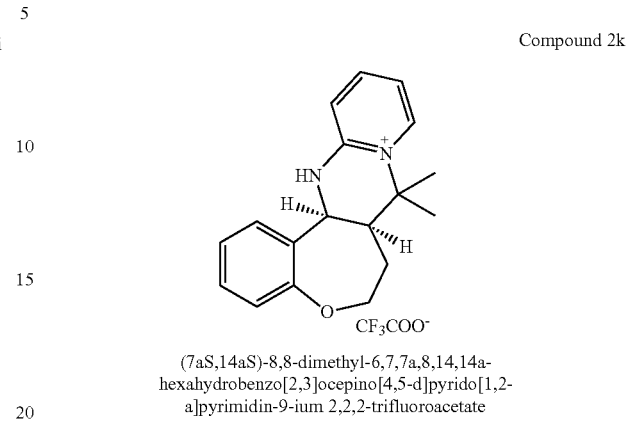

Compound 2k (7aS,14aS)-8,8-dimethyl-6,7,7a,8,14,14a-hexahydrobenzo[2,3]oxepino[4,5-d]pyrido[1,2-a]pyrimidin-9-ium 2,2,2-trifluoroacetate (Brown solid, 71 mg, yield 36%); $^1$H NMR (400 MHz, MeOH-$d_4$) δ 8.09 (d, J=7.1 Hz, 1H), 7.67 (dd, J=8.7, 7.1 Hz, 1H), 7.41 (d, J=7.6 Hz, 1H), 7.27 (td, J=7.8, 1.7 Hz, 1H), 7.05 (td, J=7.5, 0.9 Hz, 1H), 6.95 (dd, J=8.0, 1.2 Hz, 1H), 6.91-6.78 (m, 2H), 5.08 (d, J=2.9 Hz, 1H), 4.35-4.27 (m, 1H), 3.70 (dd, J=12.3, 11.3 Hz, 1H), 2.44-2.33 (m, 1H), 2.15-2.04 (m, 1H), 1.79-1.60 (m, 7H); $^{13}$C NMR (101 MHz, MeOH-$d_4$) δ 160.7, 151.8, 140.8, 134.8, 133.0, 130.7, 127.5, 123.6, 121.5, 114.8, 113.3, 71.4, 65.5, 55.2, 39.6, 30.2, 27.9, 25.3; HRMS (ESI-TOF): m/z calcd for $C_{18}H_{21}N_2O$, 281.1653, found 281.1676 [M]$^+$.

Compound 2l was prepared following the general reaction procedure iv and had the following chemical structure and characterization data:

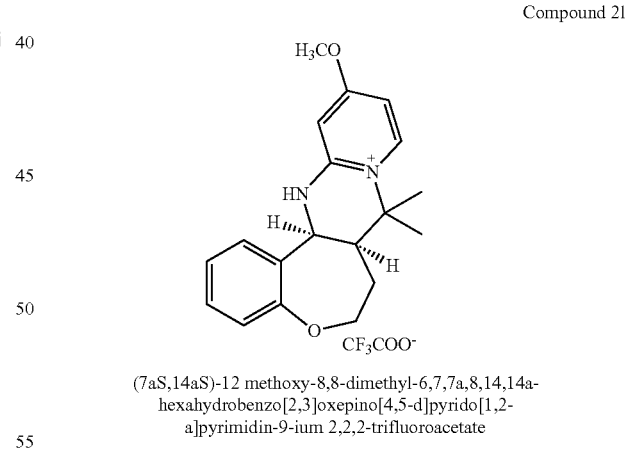

Compound 2l (7aS,14aS)-12 methoxy-8,8-dimethyl-6,7,7a,8,14,14a-hexahydrobenzo[2,3]oxepino[4,5-d]pyrido[1,2-a]pyrimidin-9-ium 2,2,2-trifluoroacetate (Off white solid, 89 mg, yield 42%); $^1$H NMR (400 MHz, MeOH-$d_4$) δ 8.05 (d, J=7.8 Hz, 1H), 7.50 (d, J=7.6 Hz, 1H), 7.42-7.34 (m, 1H), 7.17 (t, J=7.4 Hz, 1H), 7.07 (d, J=7.9 Hz, 1H), 6.58 (dd, J=7.8, 2.7 Hz, 1H), 6.31 (d, J=2.7 Hz, 1H), 5.15 (d, J=2.9 Hz, 1H), 4.44 (dt, J=12.5, 3.8 Hz, 1H), 3.93 (s, 3H), 3.87-3.76 (m, 1H) 2.50-2.40 (m, 1H), 2.24-2.21 (m, 1H), 1.91-1.73 (m, 7H); $^{13}$C NMR (101 MHz, MeOH-$d_4$) δ 168.1, 160.7, 153.4, 136.1, 132.8, 130.6, 127.7, 123.6, 121.5, 106.4, 92.4, 71.4, 64.5, 55.9, 55.2, 40.2, 29.6, 27.8, 25.3; HRMS (ESI-TOF): m/z calcd for $C_{19}H_{23}N_2O_2$, 311.1760, found 311.1766 [M]$^+$.

Compound 2m was prepared following the general reaction procedure iv and had the following chemical structure and characterization data:

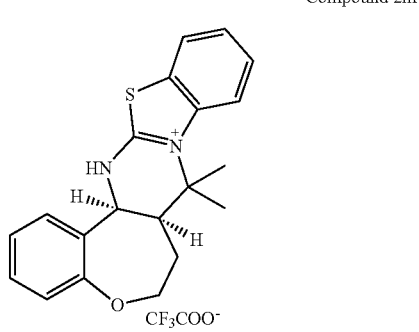

Compound 2m (7aS,15aS)-8,8-dimethyl-6,7,7a,8,15,15a-hexahydrobenzo[4,5]thiazolo[3,2-a]benzo[6,7]oxepino[5,40-d]pyrimidin-9-ium 2,2,2-trifluoroacetate (White solid, 110 mg, yield 49%); $^1$H NMR (400 MHz, MeOH-$d_4$) δ 8.04 (d, J=8.5 Hz, 1H), 7.89 (dd, J=8.0, 1.0 Hz, 1H), 7.63-7.51 (m, 2H), 7.51-7.39 (m, 2H), 7.19 (td, J=7.5, 1.1 Hz, 1H), 7.12 (dd, J=8.0, 0.9 Hz, 1H), 5.28 (d, J=1.7 Hz, 1H), 4.49 (dt, J=12.6, 3.8 Hz, 1H), 3.85 (t, J=11.3 Hz, 1H), 2.59-2.51 (m, 1H), 2.32-2.22 (m, 1H), 2.11-1.94 (m, 7H); $^{13}$C NMR (101 MHz, MeOH-$d_4$) δ 164.5, 161.0, 138.0, 132.8, 131.1, 127.4, 126.5, 125.3, 123.7, 123.3, 122.7, 121.5, 116.4, 71.7, 65.8, 57.3, 43.4, 27.6, 27.5, 24.6; HRMS (ESI-TOF): m/z calcd for $C_{20}H_{21}N_2OS$, 337.1374, found 337.1409 [M]$^+$.

Compound 2n was prepared following the general reaction procedure iv and had the following chemical structure and characterization data:

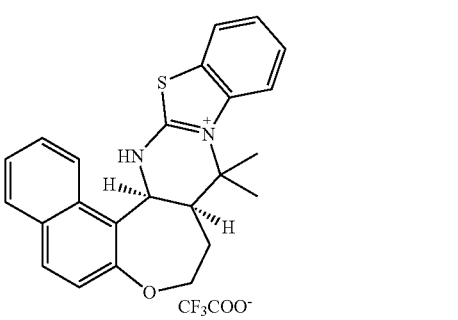

Compound 2n (9aS,17aS)-10,10-dimethyl-8,9,9a,10,17,17a-hexahydrobenzo[4,5]thiazole[3,2-a]naphtho[2′,1′:2,3]oxepino[4,5-d]pyrimidin-11-ium 2,2,2-trifluoroacetate (White solid, 107 mg, yield 43%); $^1$H NMR (400 MHz, CDCl$_3$) δ 8.16 (d, J=8.6 Hz, 1H), 7.78 (d, J=7.9 Hz, 1H), 7.67 (d, J=8.9 Hz, 1H), 7.56-7.48 (m, 1H), 7.37 (dd, J=13.3, 7.7 Hz, 2H), 7.19 (t, J=4.3 Hz, 2H), 7.12 (d, J=8.9 Hz, 1H), 7.07-7.00 (m, 1H), 5.51 (d, J=1.7 Hz, 1H), 4.49-4.34 (m, 2H), 2.61-2.52 (m, 1H), 2.51-2.35 (m, 1H), 1.89-1.71 (m, 7H); $^{13}$C NMR (101 MHz, CDCl$_3$) δ 159.5, 157.9, 139.9, 135.0, 130.2, 129.0, 128.4, 126.9, 125.1, 124.2, 123.7, 123.5, 122.2, 121.6, 120.8, 112.6, 72.5, 61.6, 54.5, 43.3, 29.4, 27.7, 24.7; HRMS (ESI-TOF): m/z calcd for $C_{24}H_{23}N_2OS$, 387.1531, found 387.1527 [M]$^+$.

Example 3

Figure 2:
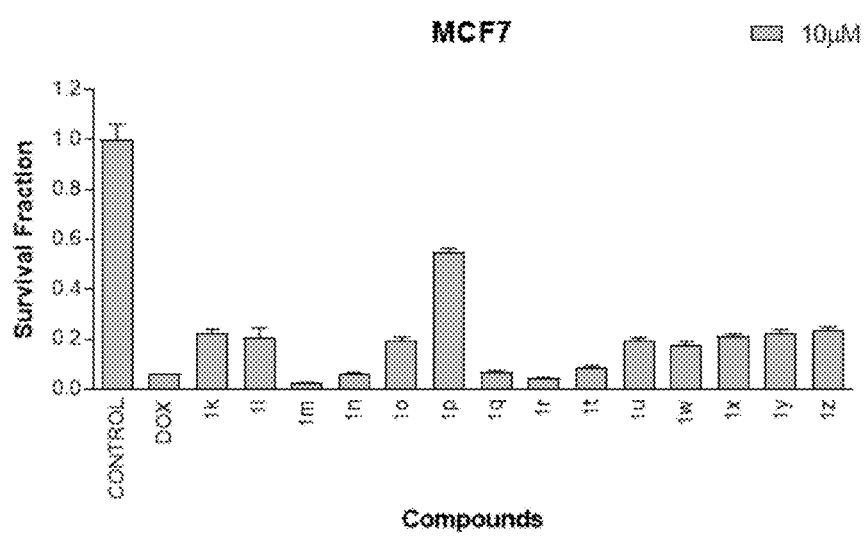
FIG. 2 is a chart showing anti-proliferative effects of various compounds on survival of breast cancer cells MCF-7, in accordance with some embodiments of the subject disclosure.

In a third experimental example, compounds synthesized in Examples 1 and 2 were initially screened for their potential anticancer activities against the cancer cell lines DU-145 and MCF7 at a concentration of 10 μM. The results of this screening process are displayed in FIG. 1 and FIG. 2.

The full dose-response curves for the representative compounds on the survival of three cancer cell lines (MCF7, SKBr3, and HCT116) was carried out and the calculated IC$_{50}$ values are presented in Table 1 (below).

TABLE 1

| | IC$_{50}$ values[a] (in μM) for the representative compounds on selected cancer cell lines | | |
|---|---|---|---|
| Compound | MCF7[b] | SKBR3[b] | HCT116[c] |
| 1m | 4.5 | 6.4 | 3.7 |
| 1n | 6.76 | 10.1 | 6.2 |
| 1q | 11.8 | 9.4 | 4.7 |
| 1r | 8.14 | 7.6 | 7.2 |
| 1t | 1.91 | 1.9 | 1.5 |
| 1x | 0.38 | 1.4 | 2.3 |
| Doxorubicin | 0.058 | 0.250 | 0.096 |

[a]50% Inhibitory concentration after 48 hours of drug treatment and the values are average of three individual experiments,
[b]breast cancer,
[c]colon cancer.

Figure 3:
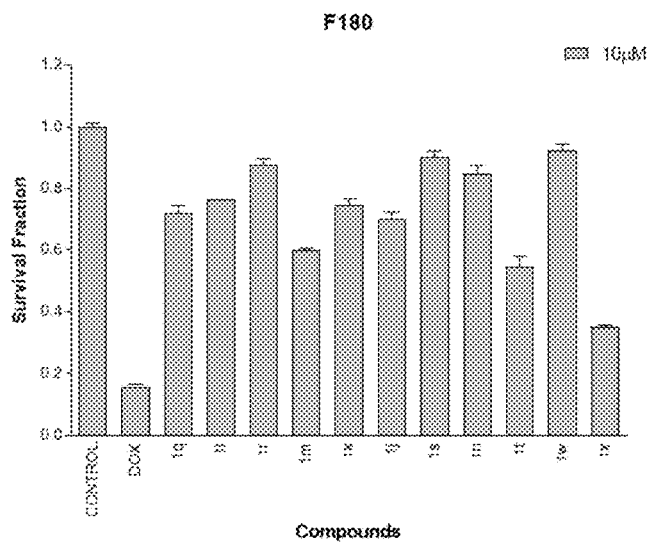
FIG. 3 is a chart illustrating the safety profiles of various compounds on normal fibroblast cells at a dose of 10 µM, in accordance with some embodiments of the subject disclosure.

In addition, the effect of these compounds on the survival of normal fibroblast strains was studied in comparison to the anticancer drug doxorubicin and the results are shown in FIG. 3. These new compounds appear to be safe on normal fibroblasts, even at high concentrations (e.g., 10 μM).

Example 4

In an effort to further understand the mechanism of action of these disclosed novel compounds, a variety of representative studies were performed on compound it.

Figure 4A:
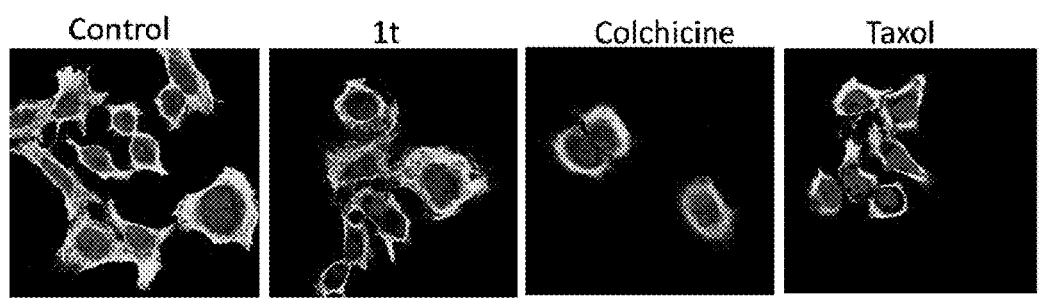
FIG. 4A shows images of immunofluorescence of tubulin polymerization in response to various treatments, including a control treatment, treatment with compound it, treatment with colchicine (positive control), and treatment with taxol, in accordance with some example embodiments of the subject disclosure. The images shown in FIG. 4A were obtained 24 hours after treatment was administered.
Figure 4B:
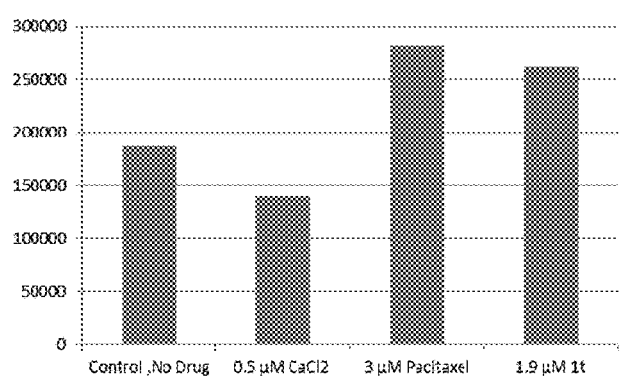
FIG. 4B shows charts illustrating the effect of various compounds on tubulin polymerization, specifically, the effects of 1.9 µM 1t, 0.5 µM $CaCl_2$), and 3 µM paclitaxel compared to results exhibited with no drug treatment. The results shown in FIG. 4B were obtained by kit method and the data in FIG. 4B is expressed as mean t SD, n=3 independent experiments.
Figure 4B:
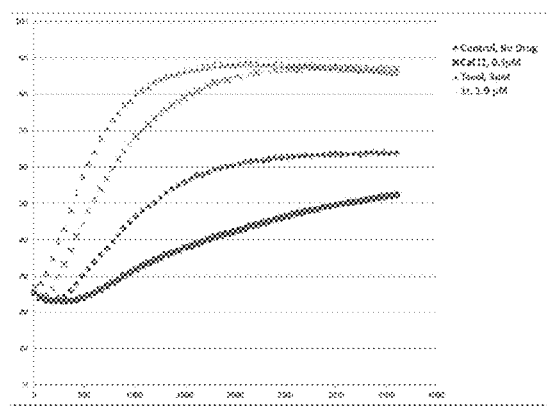

Cell synchronization and tubulin study: The antiproliferative effect of the compound it was tested on MCF7 cells which were synchronized at specific phases of the cell cycle. Cells arrested at G$_2$/M phase (18.5%) of the cell cycle were more sensitive to the compound than asynchronous cells, indicating that the target of this compound is more expressed at this phase of the cell cycle. One way of inhibiting cell proliferation in G$_2$/M phase is by altering equilibrium between polymerization and depolymerization of microtubule proteins which is required for active mitotic cell division. As evidence, compound it showed a strong inhibition to the microtubule formation in comparison to colchicine and taxol which were used as positive controls (see FIGS. 4A and 4B).

Figure 5A:
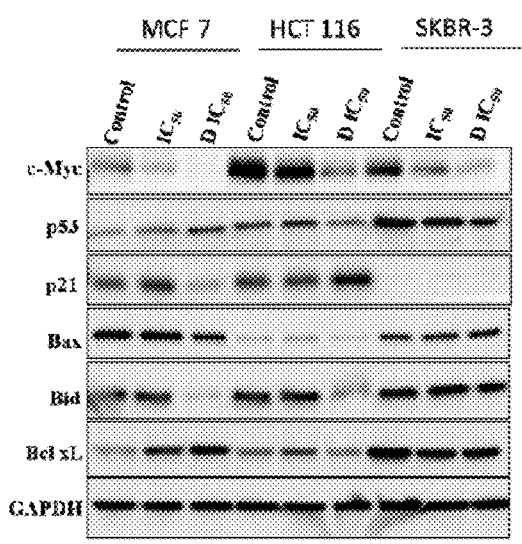
FIG. 5A shows a western blot analysis for apoptotic marker proteins along with caspases (caspase-3 and caspase-9) in MCF-7, HCT116 and SKBR3 cells.
Figure 5B:
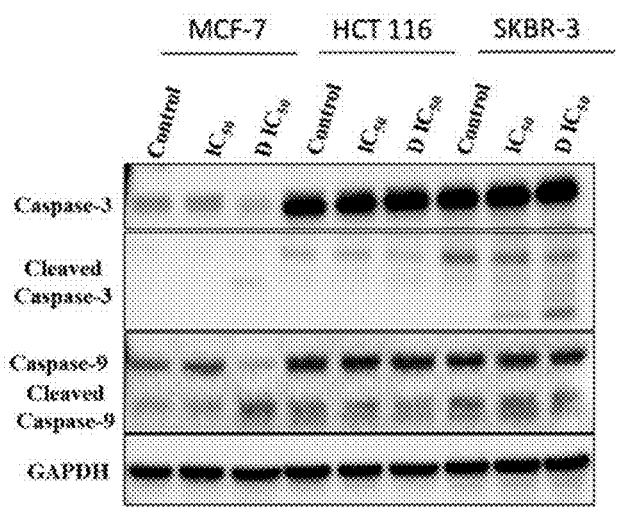
FIG. 5B shows a western blot analysis for apoptotic marker proteins in response to treatment with compound 1t at $IC_{50}$ and $DIC_{50}$ doses for 24 hours in MCF-7, HCT116, and SKBR3 cells.
Figure 6A:
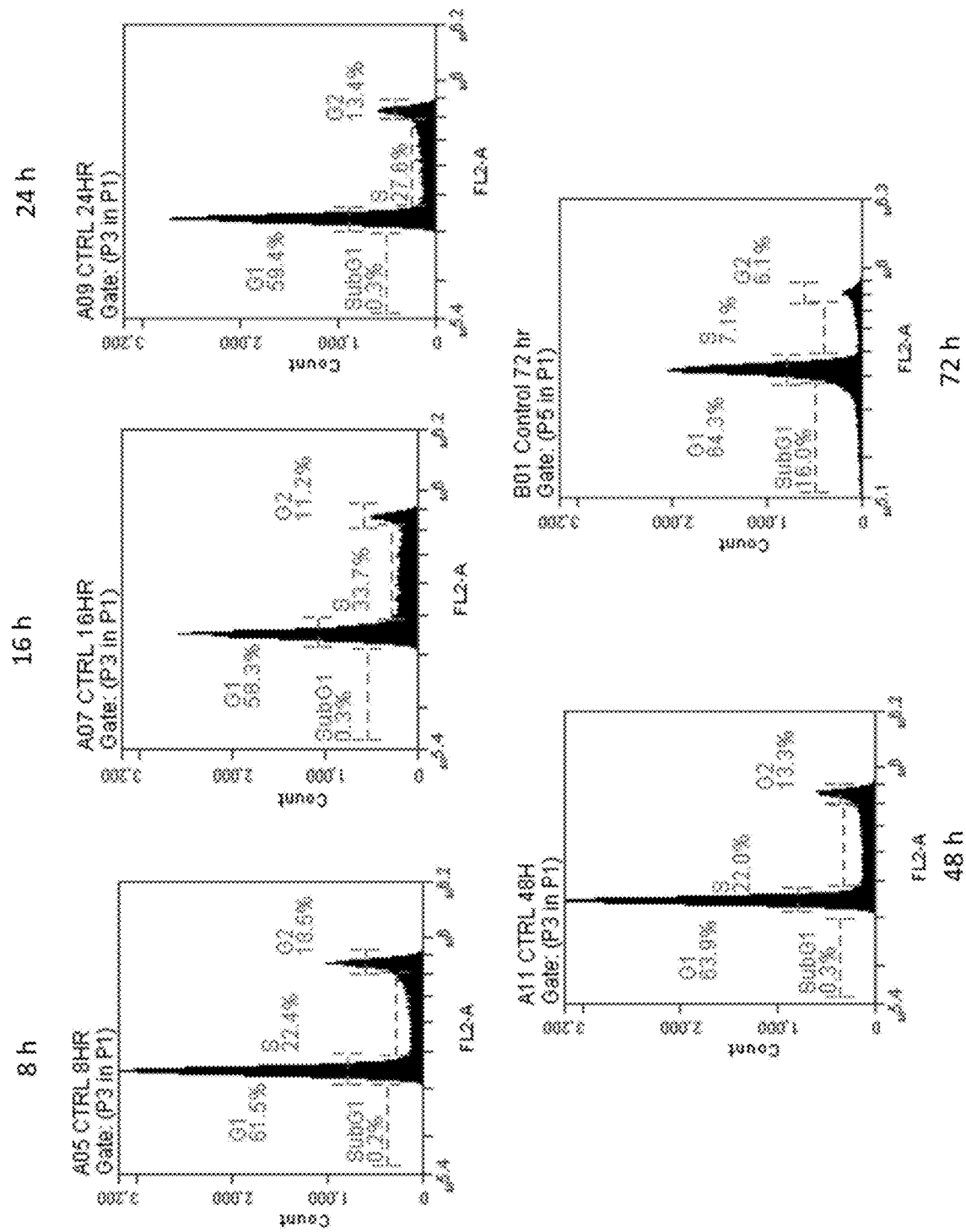
FIG. 6A shows graphs of the cell cycle arresting potentials of a control treatment in MCF7 cells after the specified treatment period (in hours).
Figure 6B:
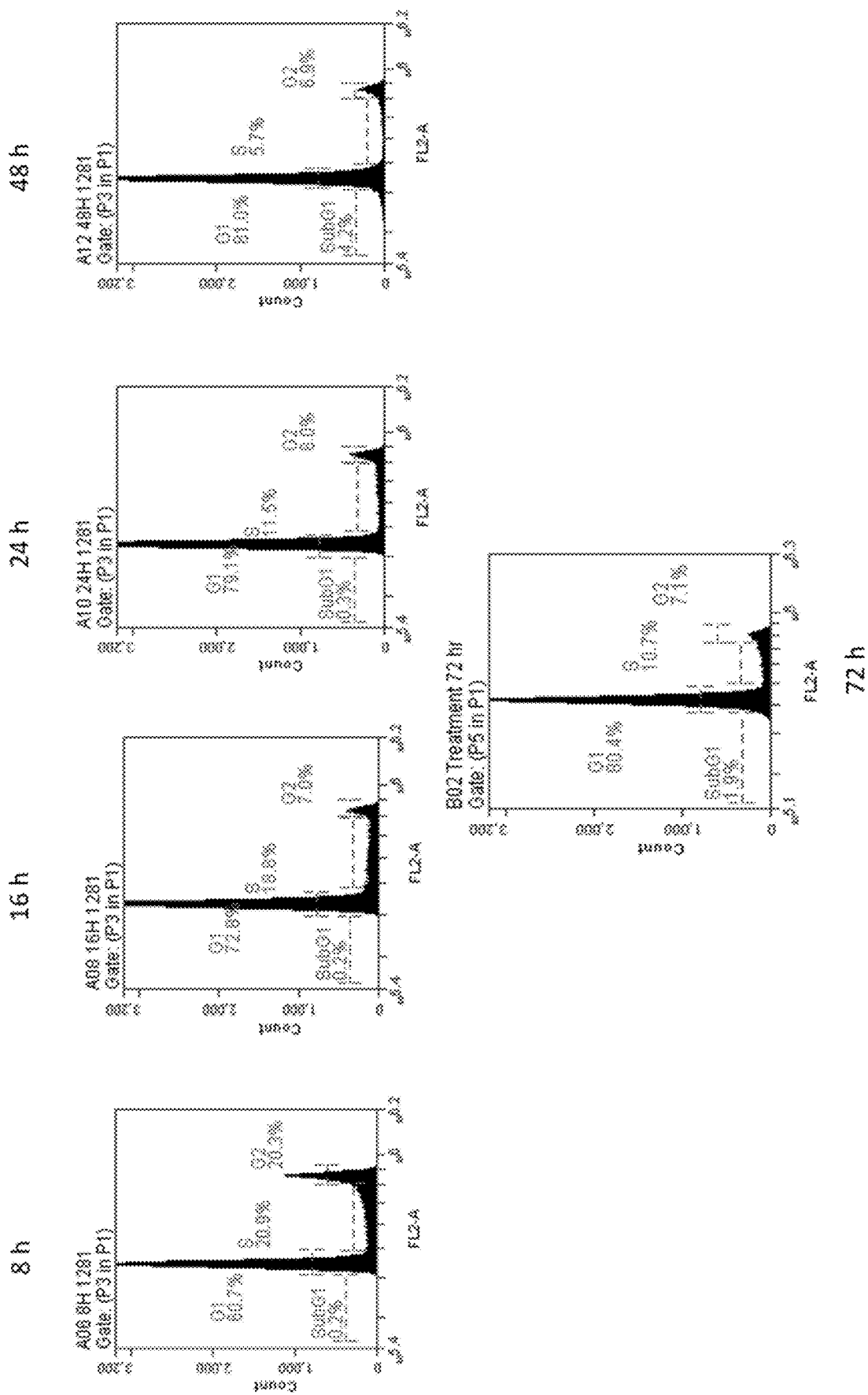
FIG. 6B shows graphs of the cell cycle arresting potentials for the treatment compound 1t in MCF7 cells after the specified treatment period (in hours).

Apoptosis studies: The molecular effect of compound it was evaluated by investigating its apoptotic (FIG. 5) and cell cycle arresting potentials (FIGS. 6A and 6B). Compound it arrests the cells at G$_0$/G$_1$ phase in MCF-7 cells (>15%) with respect to control cells after 16, 24, 48, and 72 hours of treatment. Further, the compound it displayed mitochondrial-mediated apoptotic induction with caspase-3 activation even in the aggressive multi-drug resistant breast cancer cells SKBr3.

Figure 7:
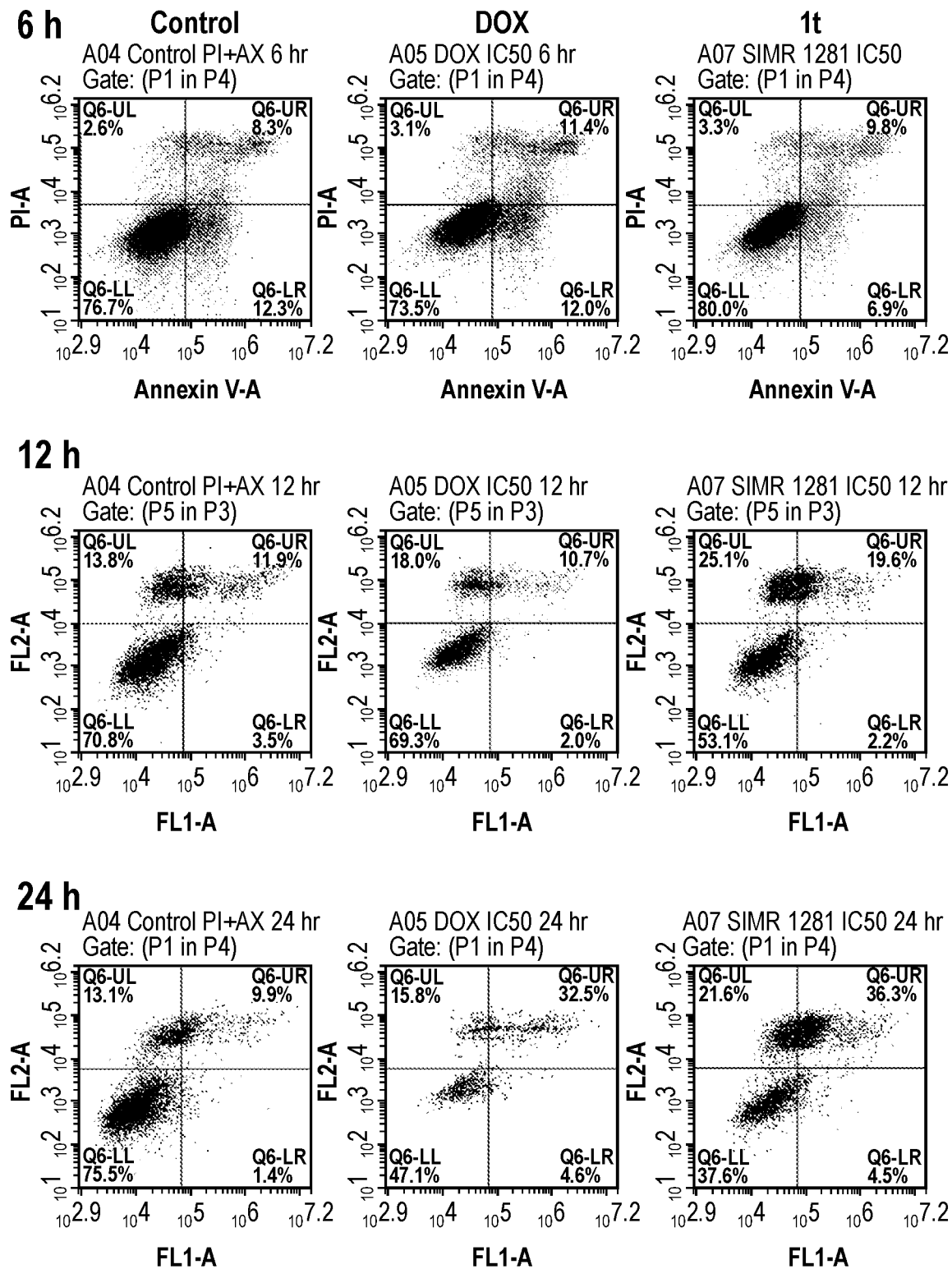
FIG. 7 shows charts illustrating apoptotic effects for the treatment compounds 1t and doxorubicin as compared to a control treatment after 6, 12, and 24 hours, as analyzed by Annexin V staining.

Pro-apoptotic and anti-apoptotic factors were found to be highly regulated in a concentration dependent manner. For instance, C-Myc oncogenic protein was found to be inhibited with compound it in all the tested cell lines. Overexpression of this oncogene could result in tumor cell proliferation and migration and therefore its inhibition may halt tumor growth. Other pro-apoptotic (Bid, Bax, caspase-3 & -9) and anti-apoptotic (Bcl-xL) proteins were also modulated by compound it as evident from western blot analysis and as confirmed by annexin V study (FIG. 7). All these results point to compound it's ability to target multiple cancer cells towards classical cell death process and arrest the cell's turn-over mechanisms.

Other findings that demonstrate the potential therapeutic uses for compound it are its effects on the expression of the tumor suppresser gene p53 and its down-stream target, p21. Compound it induced up-regulation of p53 in breast cancer cells while its down-stream protein, p21, was found to be overexpressed in HCT116 colon cancer cells. p53 is involved many cellular processes including cell cycle regulation, induction of apoptosis, and DNA repair. Regulating p53 and p21 plays a crucial equilibrium in apoptosis and compound it was found to be effective in modulating their expressions.

Figure 8:
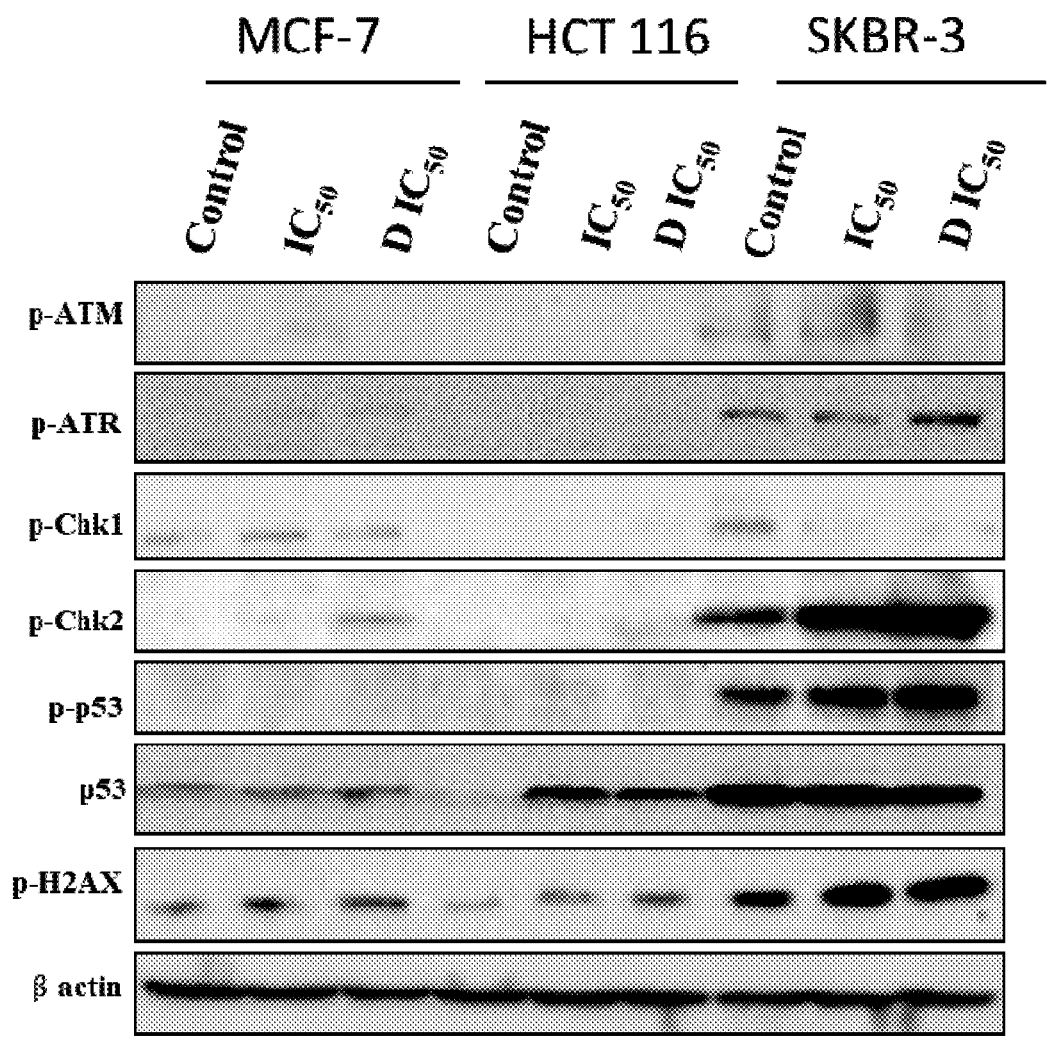
FIG. 8 shows a western blot analysis for DNA Damage Response (DDR) pathway for the treatment compound 1t at dosings of $IC_{50}$ and $DIC_{50}$ in MCF-7, HCT116, and SKBR3 cells after 24 hours.

DNA damage studies: One of the main properties of any efficient chemotherapeutic drug is to induce DNA damage in tumor cells either directly or indirectly by generating harmful DNA crosslinks, which can lead to apoptosis and impact the cell by disrupting gene function and/or impairing transcription, DNA replication, and cell proliferation. To gain additional knowledge of compound it's anticancer properties, its mechanism of action to induce DNA damage was studied in breast and colon cancer cells (FIG. 8). One of the critical post-translational modifications of chromatin is phosphorylation of multiple proteins involved in DNA damage pathway and one of the earliest events during DNA double strand break is the phosphorylation of Ser139 on the specialized histone called H2AX, which is then referred to as γ-H2AX. Compound it induced H2AX phosphorylation in SKBr3 cells after applying its $IC_{50}$ and Double $IC_{50}$ treatments.

However, recruitment of phosphatidylinositol-3-kinase (PI3K) family members to the site of DNA damage is the first step of DNA damage response mechanisms and the phosphorylation of ataxia telangiectasia-mutated (ATM) or ATM-Rad3-related (ATR) kinases often follows. Treatment with compound it phosphorylates ATR and its downstream target p53. Further, compound it also showed an elevated levels of checkpoint kinase p-Chk2 expression which co-relates to its potentials to inhibit cell cycle progression. Overall, compound it was able to induce DNA damage in an ATR-Chk2 dependent pathway in aggressive breast cancer phenotypes.

Example 5

The unique properties of compound it prompted an in-depth analysis to explore its potential novel targets. In particular, Drug Affinity Response Target Stability (DARTS) proteomic assays were performed in a dose-dependent manner and the compound it modulated the functions of the following key enzymes which are upregulated in cancer cells: thioredoxin reductase, transketolase, cytosol aminopeptidase, glutathione reductase, inositol-3-phosphate synthase, transferrin receptor proteins, and dihydrolipoamide dehydrogenase (see FIGS. 9, 10, 11, 12, 13, 14, and 15, respectively).

Figure 9:
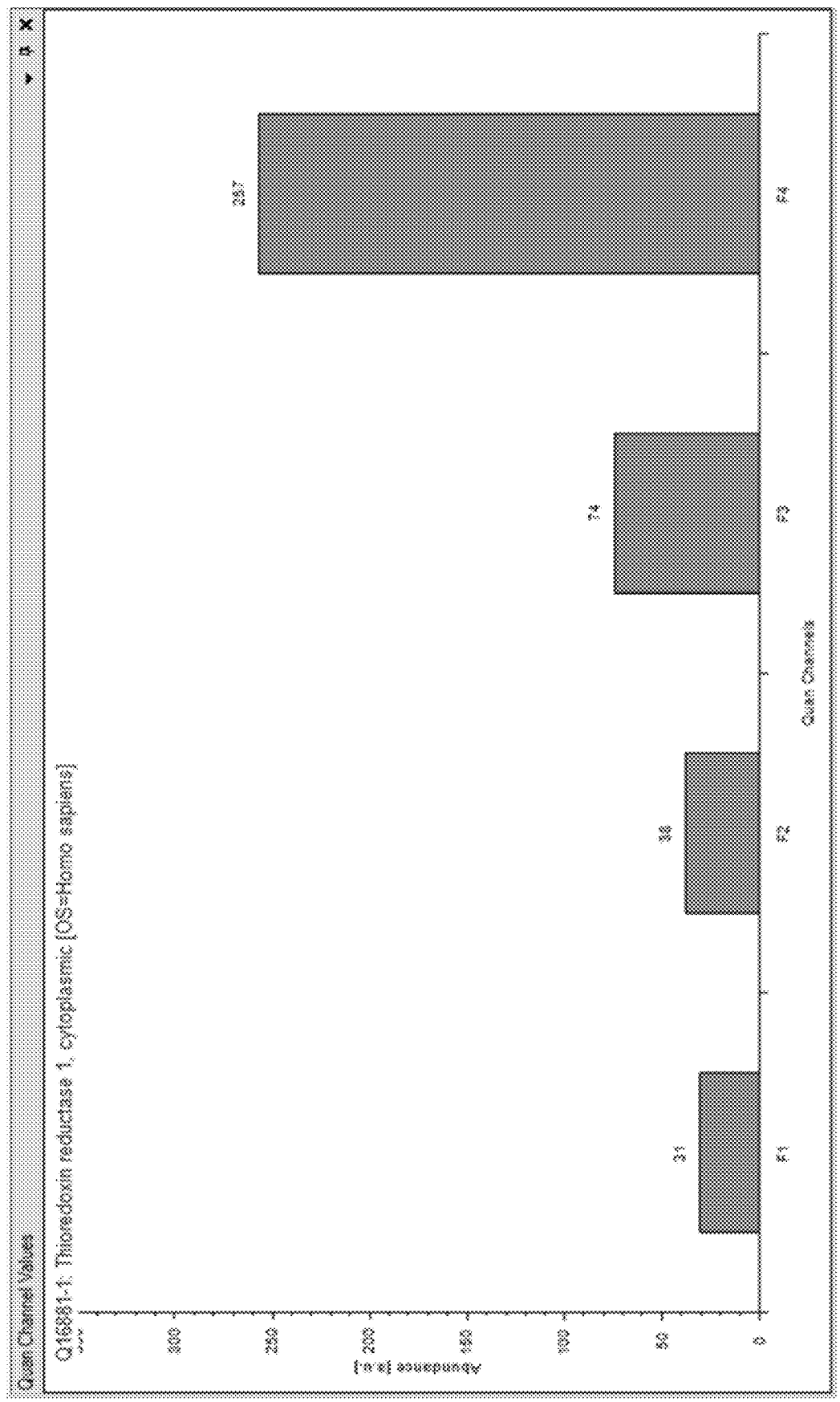
FIG. 9 shows a DARTS analysis of the inhibiting potential of different doses of the compound 1t on thioredoxin reductase.

Mammalian thioredoxin reductases (TrxRs) are selenocysteine-containing homodimericflavin enzymes that catalyze the NADPH-dependent reduction of oxidized thioredoxins. Some evidence suggests that increased TrxRs levels may facilitate cancer development due to its growth promoting and apoptosis inhibiting functions. Therefore, inhibiting this enzyme should form the foundation of a novel anticancer lead drug candidate. Many drug companies around the world are trying to design drugs that target this enzyme, however, until now there is no clinical anti-cancer drug that specifically targets TrxR although some drugs have been reported to inhibit TrxR to varying extents. Promisingly, compound it exhibited concentration-dependent modulation of TrxR with the highest effect observed at 1 µM (FIG. 9). One of the hurdles in developing a successful TrxR inhibitor is its cross reactions with thiols present inside the cells. Unlike other proposed metal complexes and Michael acceptors, compound it does not have any appropriate reactive groups (such as selenol or a sulfhydryl group) that can undergo cross reactivity with thiol groups. Moreover, according to many reports, inhibiting excessive TrxR levels will also aid in pathogenesis of Parkinson's disease as well as Alzheimer's disease. On the other hand, increased aminopeptidases are typically observed in many cancer tissues and play a key role in tumor cell proliferation, angiogenesis, and tumor invasiveness by regulating extracellular matrix degradation and cell signaling and recognition. Similar to TrxR 1, compound it was also found to targets cytosolic aminopeptidase in a dose-dependent manner.

Similarly, deregulated inositol metabolism has been observed in a number of diseases, including cancer, where inositol modulates different critical pathways in disease progression. Moreover, it is expressed consistently in bipolar disorders and Alzheimer's diseases. Compound it has shown a dose-dependent affinity to bind to the active site of this enzyme and regulates its function. Likewise, the role of glutathione reductase is well known in cancer progression and chemoresistance. The equilibrium between the glutathione disulphide ratio is critical not only in cancer progression but also in increased oxidative stress which can lead to other disorders. Hence, regulation of these metabolic enzymes could be accomplished by a complete drug which can overcome the issues in chemotherapy, especially when targeted through receptors like transferrin. Compound it displayed higher affinity to transferrin receptors, which can enable it to target cancer cells alone by modulating expression of other key enzymes, which appeared to be up-regulated in tumor cells.

Figure 10:
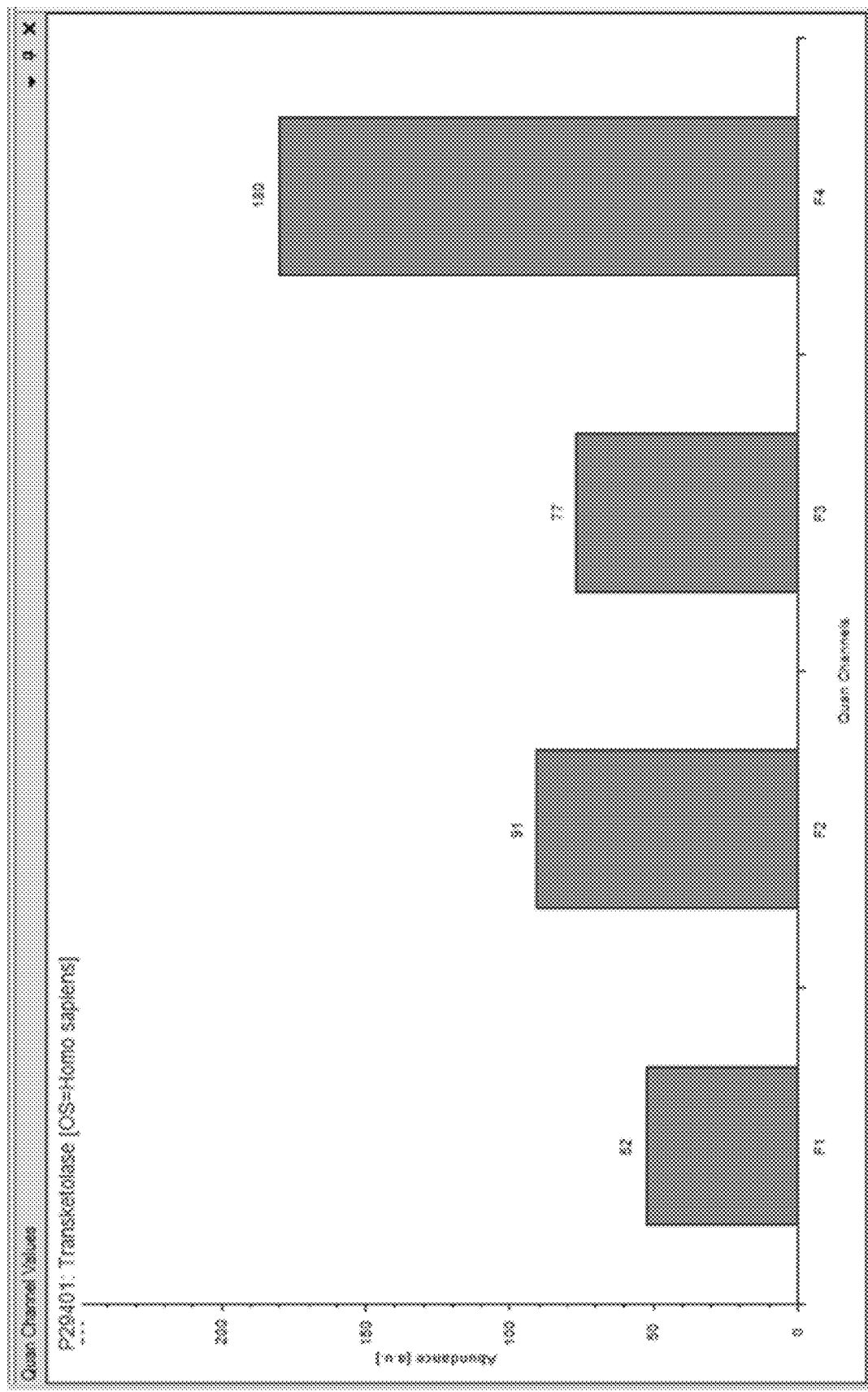
FIG. 10 shows a DARTS analysis of the inhibiting potential of different doses of the compound 1t on transketolase.
Figure 11:
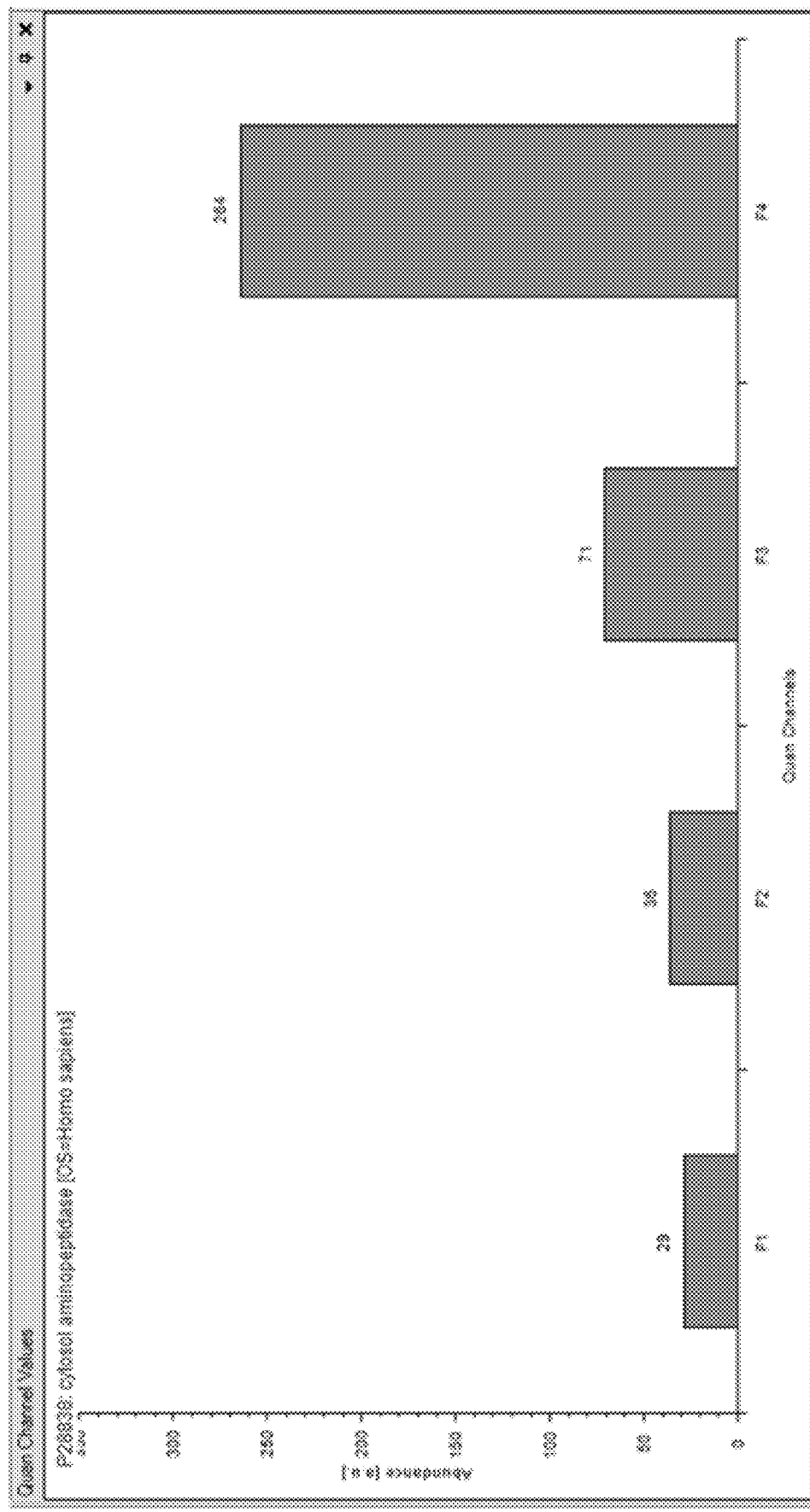
FIG. 11 shows a DARTS analysis of the inhibiting potential of different doses of the compound 1t on cytosol aminopeptidase.
Figure 12:
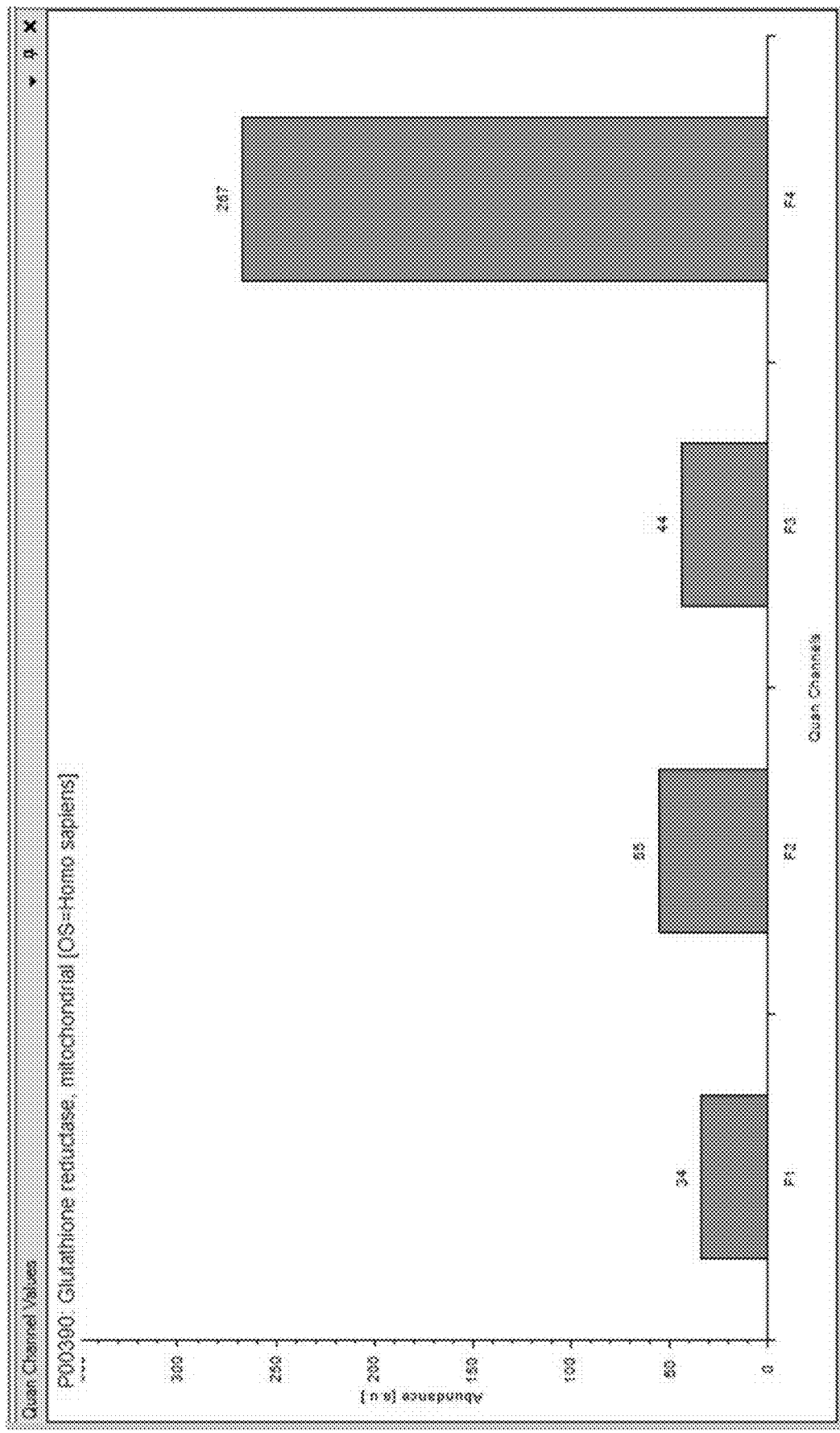
FIG. 12 shows a DARTS analysis of the inhibiting potential of different doses of the compound 1t on glutathione reductase.
Figure 13:
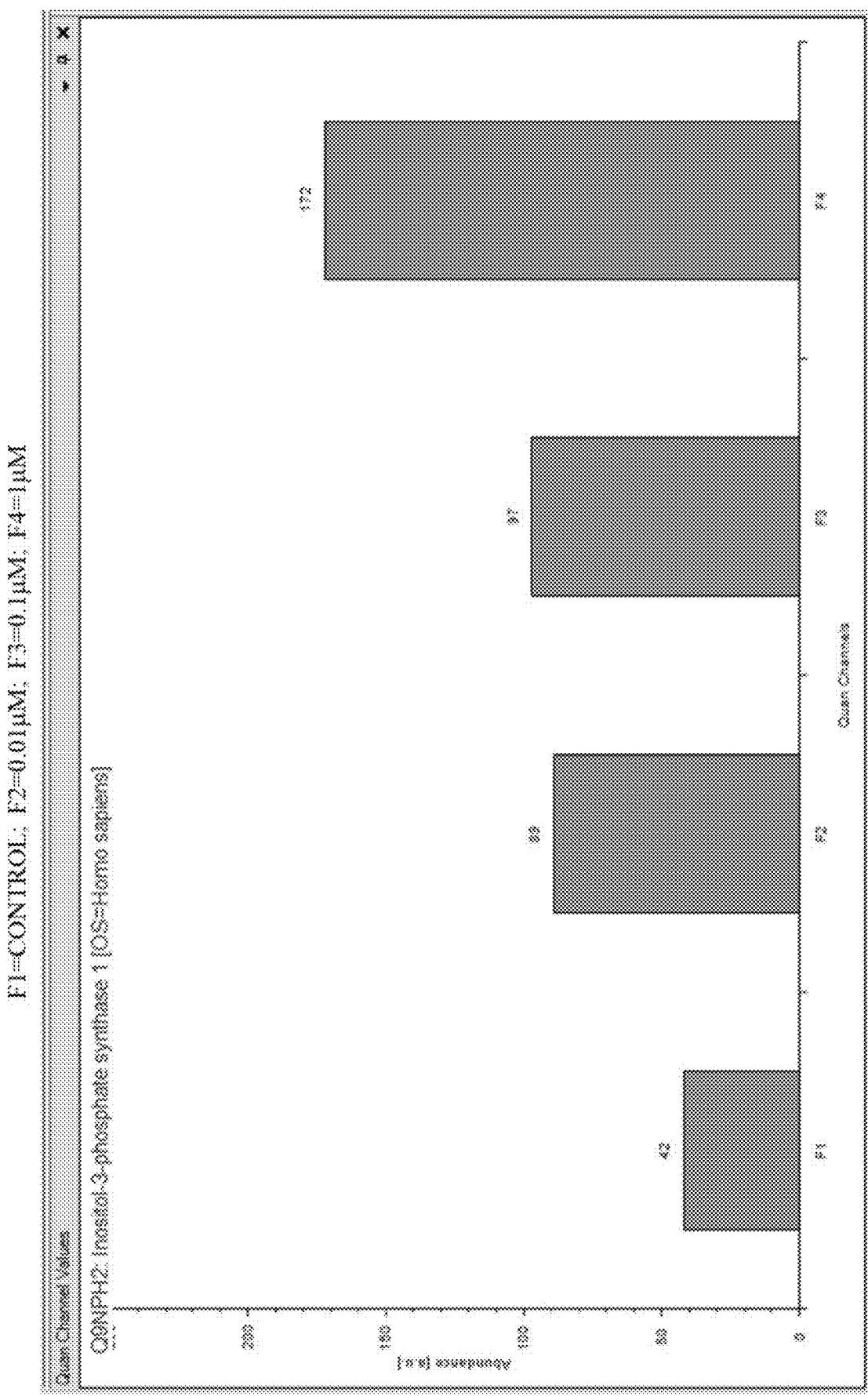
FIG. 13 shows a DARTS analysis of the inhibiting potential of different doses of the compound 1t on inositol-3-phosphate synthase.
Figure 14:
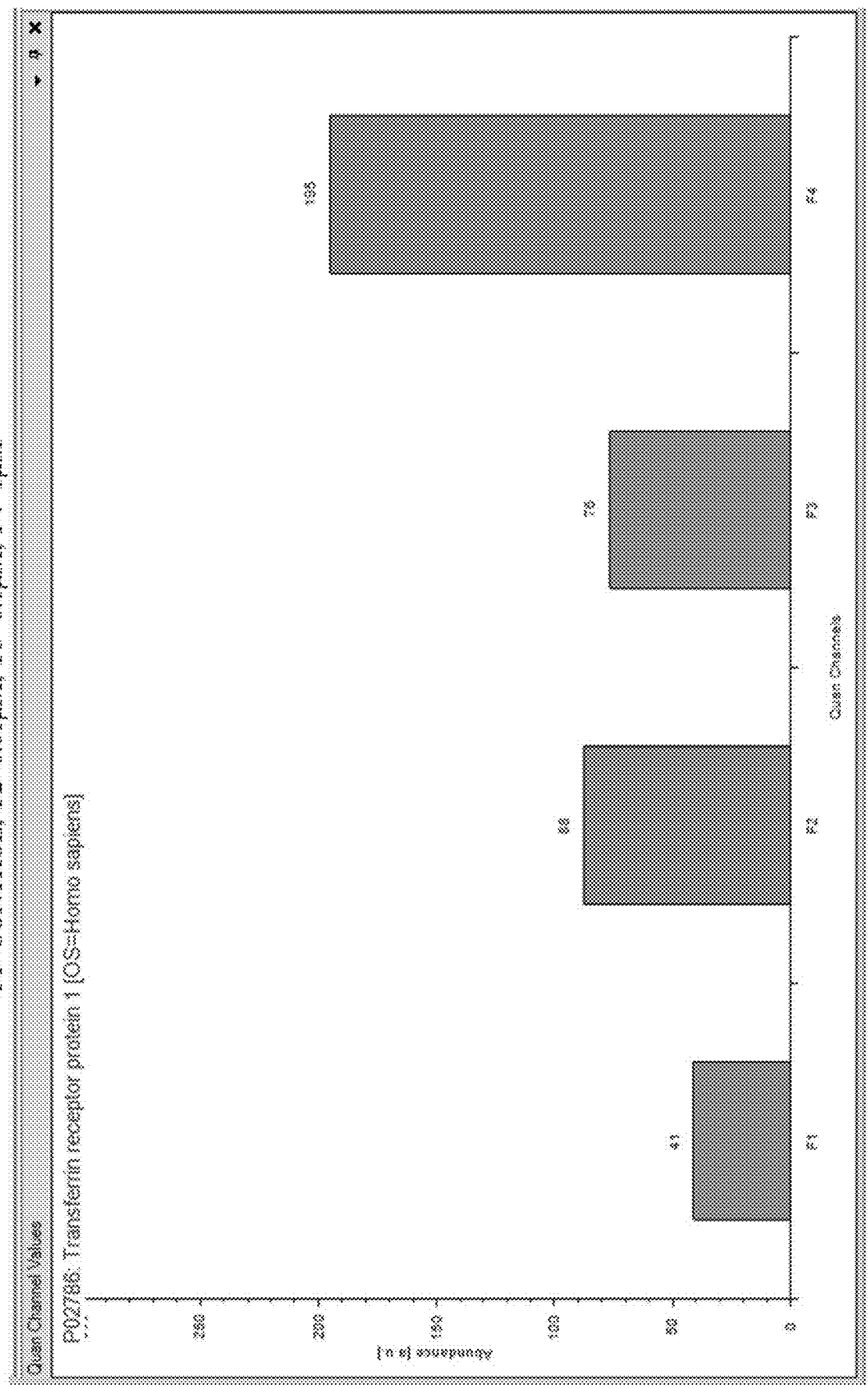
FIG. 14 shows a DARTS analysis of the inhibiting potential of different doses of the compound 1t on transferrin receptor proteins.
Figure 15:
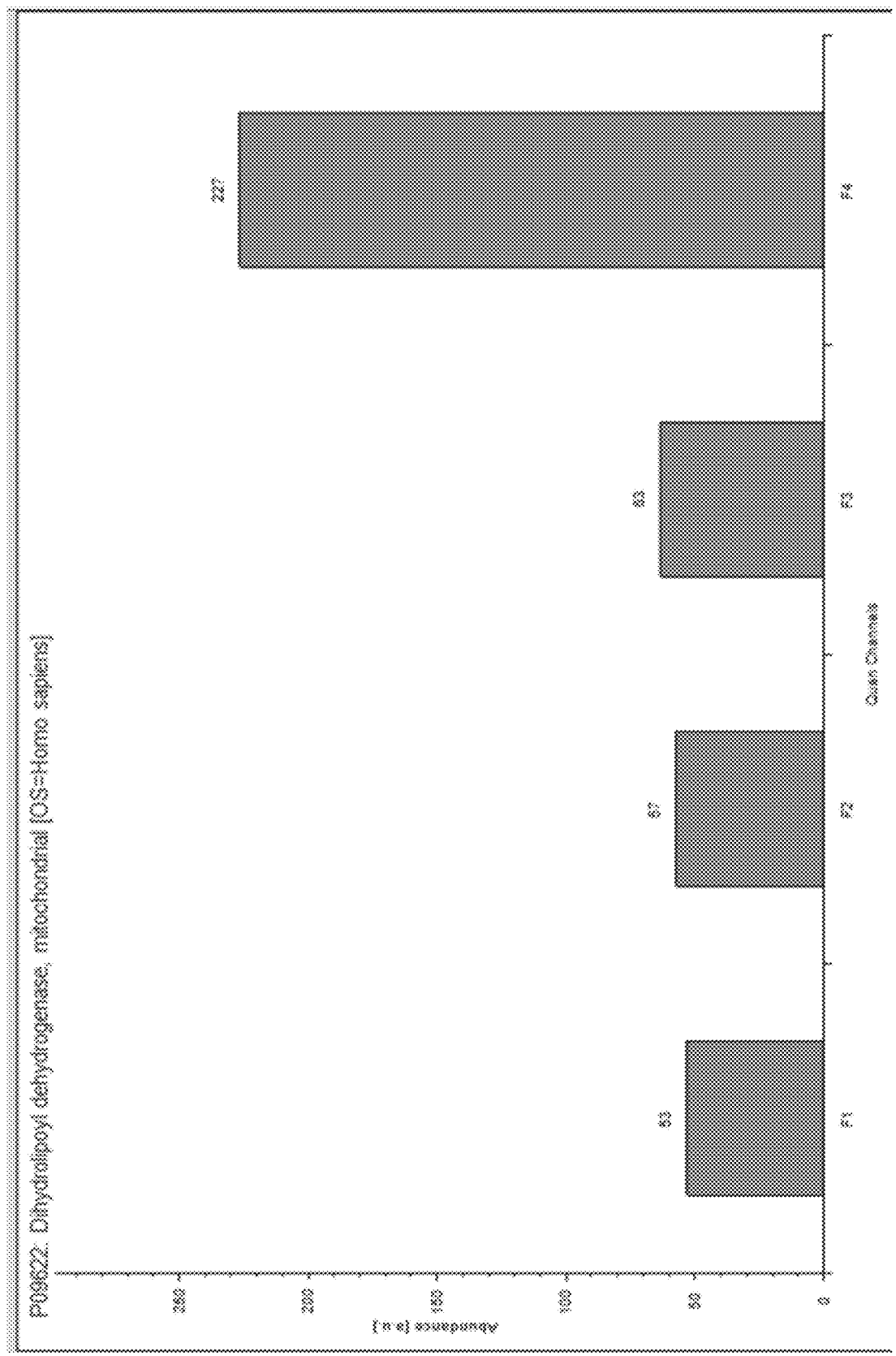
FIG. 15 shows a DARTS analysis of the inhibiting potential of different doses of the compound 1t on dihydrolipoyl dehydrogenase.
Figure 16:
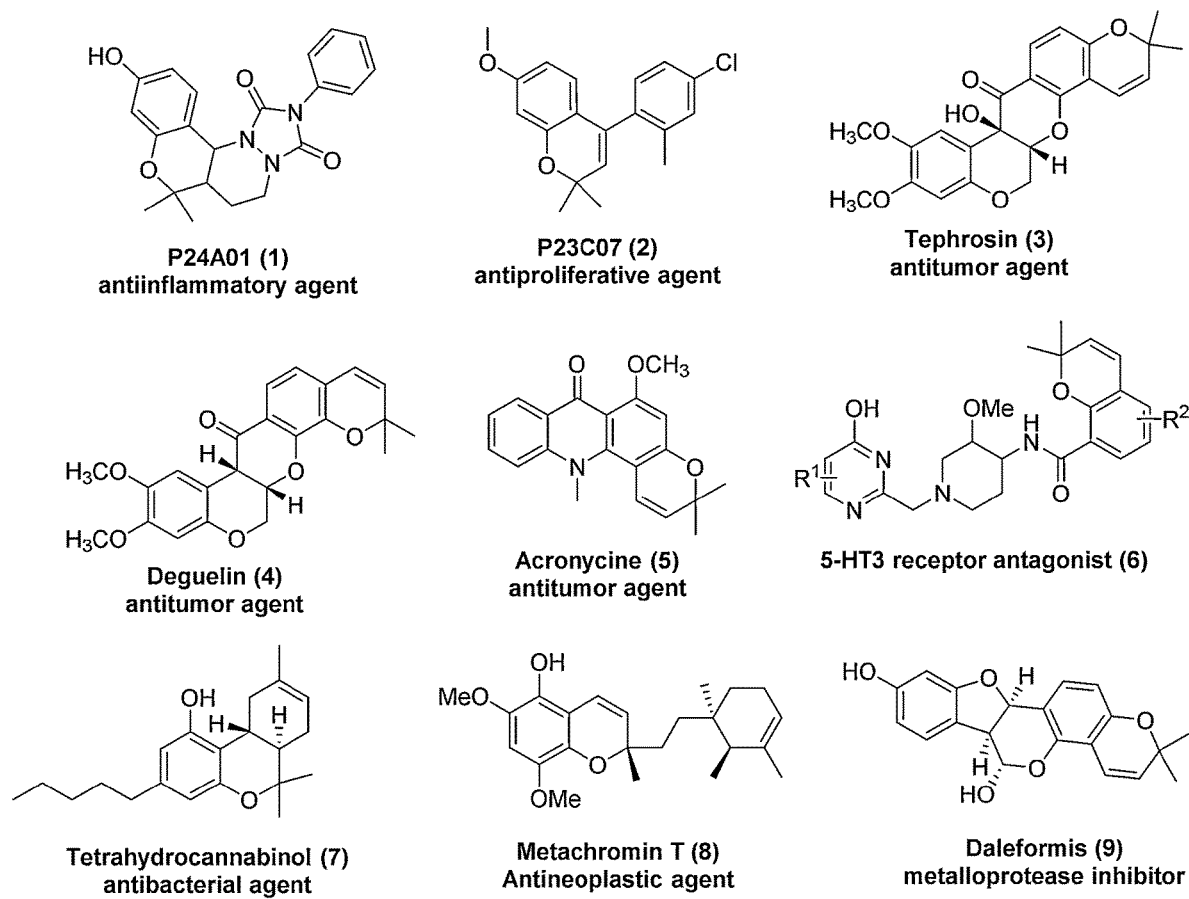
FIG. 16 shows the chemical structures of exemplary bioactive compounds with a benzopyran skeleton, in accordance with some embodiments of the subject disclosure.

The enzyme transketolase (TKT) was found to be yet another target for the compound it activity. As TKT reaction plays a pivotal role in pentose phosphate pathway, inhibition of TKT will suppress the pentose phosphate pathway and interrupt the synthesis of coenzymes, ATP, CoA, NAD(P)+, FAD, RNA, and DNA in cancer cells. The over-expressed TKT is reported in many cancer cells, tissues, and patients, wherein it regulates proliferation and viability. A strategy of silencing TKT has shown significant effect in reducing tumor burden in gastric cancer cells. Recent studies have shown that targeting TKT has clinical relevance in cancer therapy, as it can counteract the effect of oxidative stress, a critical factor in cancer development. The initial DART assay showed a strong affinity for compound it on this enzyme in a dose-dependent manner and indicates compound it could be used for targeting this enzyme to inhibit cancer development (as shown in FIG. 10).

Dihydrolipoamide dehydrogenase (DLD) is a mitochondrial enzyme involved in metabolic process that is encoded by the DLD gene. Not many studies have been done to identify the direct involvement of this enzyme in cancers.

However, a deregulated level of DLD may modulate mitochondrial-mediated diseases and may impair normal metabolic processes. Compound 1t also regulates this enzyme and may have an impact on inhibiting the energy required for tumor cell growth and metabolism (see FIG. 15). The presently disclosed data is encouraging and indicates compound 1t may potentially be used to target multiple key enzymes that are involved in tumor development and progression.

General Materials and Methods of the Present Disclosure

Unless otherwise stated, the following materials, techniques, and methods were used in the experiments described herein.

Chemistry

Purchased chemical reagents and anhydrous solvents were used without further purification. Solvents for extraction and column chromatography were distilled prior to use. TLC analysis was performed with silica gel plates (0.25 mm, 60 F254) using iodine and a UV lamp for visualization. $^1$H and $^{13}$C NMR experiments were performed on a 400 MHz instrument, respectively. Chemical shifts are reported in parts per million (ppm) downstream from the internal tetramethylsilane standard. Spin multiplicities are described as s (singlet), bs (broad singlet), d (doublet), dd (double doublet), t (triplet), q (quartet), or m (multiplet). Coupling constants are reported in Hertz (Hz). ESI mass spectrometry was performed on a Q-TOF high resolution mass spectrometer or Q-TOF Ultim LC-MS.

Chemicals and Cell Culture

Dulbecco's Modified Eagles Medium (DMEM), RPMI 1640 medium and propidium iodide (PI) were purchased from Sigma Aldrich (Darmstadt, Germany). For western blot, the antibodies; c-Myc, $p^{53}$, $p^{21}$, Bax, Bid, BclxL, GAPDH, caspase-3, caspase-9, p-ATM, p-ATR, p-Chk1, p-Chk2, and p-H2AX along with respective mouse/rabbit secondary antibodies were purchased from Cell Signaling Technology (Danvers, MA, USA). FITC Annexin V Apoptosis kit was purchased from BD Biosciences (New Jersey, USA). All other chemicals and solvents used were of standard analytical grade. The stock solutions of SIMR compounds were made in 100% DMSO and working solutions for treatments never exceeded >1% DMSO. The cell lines were gifted from Radiobiology and Experimental Radio Oncology lab, University Cancer Center, Hamburg University, Hamburg, Germany. F180 and HCT116 cells were cultured in DMEM media while MCF-7 and SKBR3 cells were cultured in RPMI along with 10% FBS and 5% $CO_2$ in a humidified incubator at 37° C. The cells were grown on polystyrene T-75 (75 cm$^2$) culture flasks and all the experiments were performed at ~70% cell confluency.

Sulforhodamine B (SRB) Assay

SRB assay was performed on DU-143 and MCF-7 cells in order to find out the sub-lethal dosage ($IC_{50}$) of the synthesized compounds based on reported method with minor modifications. Briefly, 1×10$^4$ cells were seeded in a 96-well plate overnight and were treated with different concentrations of compounds and incubated further for 48 hours. The wells which were devoid of any treatment served as controls. After the treatment time, the plates were incubated with 50% trichloroacetic acid (TCA) at 4° C. for 1 hour. The cells were then washed, dried and exposed to 1% acetic acid for short period. Two hundred microliters of 10 mMtris base solution was then added with 10 min incubation after drying the plates and the OD was read at 492 nm by using a Multiskan™ GO (Thermo Scientific, USA) microplate Spectrophotometer.

Western Blot

The MCF-7, SKBR3 and HCT116 total cell lysate were prepared after 24 hours of treatment with compound it at $IC_{50}$ and $DIC_{50}$ doses by using 1× laemmli buffer. Total protein concentration was then estimated for each sample and 15-30 μg of protein lysate were loaded equally on 12% SDS-PAGE gel in order to detect various proteins expression levels. In short, the membrane was incubated with different primary antibodies (as mentioned in above section) (1:1000) overnight after blocking with 5% non-fat milk solution for 1 hour. The membrane was then re-probed with respective mouse/rabbit secondary antibodies (1:2000) for 1 h, and later developed by enhanced chemiluminescence (ECL) method by using a Chemidoc MP (BioRad, Germany).

Apoptosis by Annexin V Staining

The apoptotic level was measured using a kit method as per supplier's protocol. The MCF-7, SKBR3, and HCT116 cells (3×10$^6$) were seeded overnight in a T75 cm$^2$ flask for attaining 70% confluency. The cells were treated with IC50 doses of SIMR1281 along with doxorubicin for 6, 12, and 24 hours. The cells were then scrapped off and washed twice with ice cold PBS. 2×10$^6$ cells were counted and re-suspended in 1 mL of binding buffer (1×). 5 μL of FITC Annexin V and PI was then added to 100 μL of cell suspension and incubated at dark for 15 min. 400 μL of IX binding buffer was finally added to the cells and analyzed immediately by using by a flow cytometer (BD, Accuri C6).

Cell Cycle Analysis

Cell cycle arresting potentials of compound it were analyzed by an already established protocol with minor modifications. In brief, 3×10$^6$ cells of MCF-7, SKBR3, and HCT116 were seeded and incubated overnight in a T75 cm$^2$ flask before treating with $IC_{50}$ dose of compound it for 2, 4, 8, 16, 24, 48, and 74 hours. The cells which were devoid of any treatments served as controls for each group. After respective treatment hours, the cells were washed two times with PBS and fixed with ice cold ethanol (70%) overnight. The cells were then washed two times with cold PBS and 1×10$^6$ cells were then counted and incubated with 1 ml RNAase (100 μg/mL) for 30 min at 37° C. The cell pellet was further added with 200 μl of propidium iodide (50 μg/mL) and immediately analyzed by a flow cytometer (BD, Accuri C6).

Immunofluorescence Assay

An immunofluorescence method is used for detecting tubulin polymerization effect of compound 1t. The cells (5×10$^4$/well) were plated overnight on coverslips on a six well plate and treated with $IC_{50}$ concentration of compound 1t, taxol and colchicine for 24 hours. After treatment, the cells were rinsed twice with PBS, fixed with 3.7% paraformaldehyde, and permeabilized with 0.1% Triton X-100. The cells were then blocked with 1% BSA in PBS for 1 hour before further incubation with anti-p-tubulin mouse monoclonal antibody overnight at 4° C. (Cell Signaling, San Francisco, CA). The cells were incubated further with Alexa Fluor® 488 secondary antibodies (Abcam, UK), after being washed with PBS for 1 hour at dark. The cellular microtubules were observed with a Nikon® Eclipse Ti™ Microscope (Japan).

In Vitro Tubulin Polymerization Assay

Tubulin polymerization was measured in vitro using the Tubulin Polymerization Assay kit (Cytoskeleton, Denver, CO). In Brief, 2 mg/mL Porcine Tubulin was dissolved in Buffer 1 (80 mM PIPES, 2 mM MgCl2, 0.5 mM EGTA pH 6.9, 10 μM fluorescent reporter, 1 mM GTP, 15% glycerol) to a final concentration of 10 mg/mL. Then tubulin solution was transferred to a pre-warmed 96-well plate that contained test compounds, 3 uM paclitaxel or control buffer. The polymerization of tubulin was monitored as fluorescence at 37° C. for 60 min, and the reading speed was programmed at 1 cycle/min with excitation and emission wavelengths of 360 and 450 nm, respectively, using the Varioskan® Flash spectral scanning multimode reader (Thermo Fisher Scientific™).

Immunofluorescence Microtubule Detection

A549 cells ($5\times10^4$/well) plated on coverslips on 6 well plate were treated with indicated concentration of test compounds for 24 hours. After treatment, cells were rinsed twice with PBS, fixed with 3.7% paraformaldehyde, and permeabilized with 0.1% Triton X-100. Cells then were blocked with 1% BSA in PBS for 1 hour before further incubation with anti-β-tubulin mouse monoclonal antibody overnight at 4° C. (#86298, Cell Signaling, San Francisco, CA). Cells were incubated with Alexa Fluor® 488 secondary antibodies (Abcam), after being washed with PBS for 1 hour at dark room. Cellular microtubules were observed with an Nikon® Eclipse Ti™ microscope (Japan).

DARTS Assay

A DARTS assay was used to assess the binding of compound 1t. HEK293T cells were lysed using M-PER (Thermo Scientific, Inc.) supplemented with protease and phosphatase inhibitors (Lysis buffer). 4.7 mg/mL of protein and TNC buffer (10 mM Tris, 140 mMNaCl, 5 mM $CaCl_2$)) was added, compound it was diluted in DMSO to 3 different concentrations (0.01 µM, 0.1 µM, 1 µM) and incubated for one hour at room temperature. Trypsin (Promega) was added and incubated for 3 hours at 37° C. Thereafter, M-PER lysis buffer was added and the samples were concentrated with Microcon 10K centrifugal filters. The proteins were identified by gel electrophoresis liquid chromatography mass spectroscopy (GelLCMS).

What is claimed is:

1. A compound having the following formula:

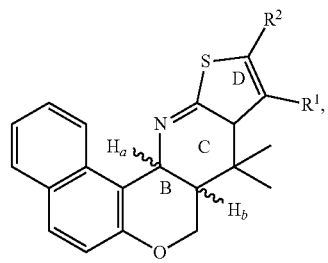

wherein:

$H_a$ and $H_b$ are each hydrogen atoms;

$R^1$ is a phenyl ring which may be unsubstituted or substituted with 1, 2, 3, or 4 substituents independently selected from the group consisting of: F, Cl, I, CN, $R^3$, $OR^3$, $SR^3$, $N(R^3)_2$, $C(O)R^3$, $C(O)OR^3$, $SO_2R^3$, $NR^3SO_2R^3$, and $SO_2N(R^3)_2$;

$R^2$ is hydrogen or alkyl; and $R^3$ is hydrogen or is selected from the group consisting of: a $C_{1-6}$ aliphatic group; $-CX_3$, $-CHX_2$, or $-CH_2X$, wherein X is chloro, fluoro, bromo, or iodide: a monocyclic 3-8 membered saturated or partially unsaturated ring having 0-4 heteroatoms independently selected from nitrogen, oxygen, or sulfur, aryl ring, or heteroaryl ring having 1-4 heteroatoms independently selected from nitrogen, oxygen, or sulfur; a bicyclic 8-10 membered saturated or partially unsaturated ring having 0-5 heteroatoms independently selected from nitrogen, oxygen, or sulfur, aryl ring, or heteroaryl ring having 1-5 heteroatoms independently selected from nitrogen, oxygen, or sulfur, or a pharmaceutically acceptable salt thereof.

2. The compound of claim 1, wherein:

$R^3$ is selected from the group consisting of: $-CX_3$, $-CHX_2$, and $CH_2X$, wherein X is chloro, fluoro, bromo, or iodide.

3. A process for the preparation of the compound of claim 1, the process utilizing a compound of formula I and a compound of formula II as starting materials, wherein:

formula I is:

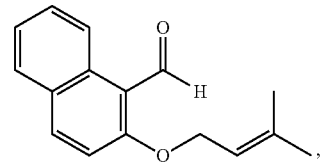 [SMILES: CC(C)=CCOc1ccc2ccccc2c1C=O]

formula II is:

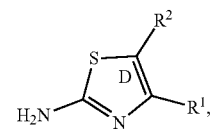

wherein:

$R^1$ is a phenyl ring which may be unsubstituted or substituted with 1, 2, 3, or 4 substituents independently selected from the group consisting of: F, Cl, I, CN, $R^3$, $OR^3$, $SR^3$, $N(R^3)_2$, $C(O)R^3$, $C(O)OR^3$, $SO_2R^3$, $NR^3SO_2R^3$, and $SO_2N(R^3)_2$;

$R^2$ is hydrogen or alkyl, and $R^3$ is hydrogen or is selected from the group consisting of: a $C_{1-6}$ aliphatic group; $-CX_3$, $-CHX_2$, or $-CH_2X$, wherein X is chloro, fluoro, bromo, or iodide; a monocyclic 3-8 membered saturated gr partially unsaturated ring having 0-4 heteroatoms independently selected from nitrogen, oxygen, or sulfur, aryl ring, or heteroaryl ring having 1-4 heteroatoms independently selected from nitrogen, oxygen, or sulfur; a bicyclic 8-10 membered saturated or partially unsaturated ring having 0-5 heteroatoms independently selected from nitrogen, oxygen, or sulfur, aryl ring, or heteroaryl ring having 1-5 heteroatoms independently selected from nitrogen, oxygen, or sulfur, and the process comprises:

a. mixing the compound of formula I and the compound of formula II in a polar aprotic solvent in the presence of a metal triflate to form an imine compound of formula III, wherein formula III is:

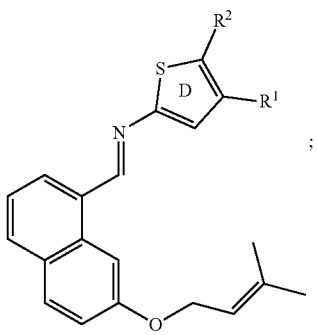

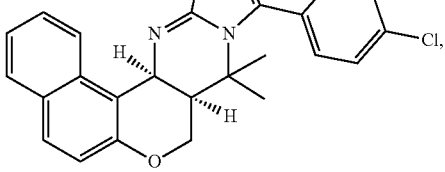

b. heating to a temperature between 40° C. and 100° C. for between 12 hours and 16 hours to form the compound of the formula of claim 1 in a crude reaction mixture;
c. removing the polar aprotic solvent under vacuum to dry the crude reaction mixture; and
d. purifying the crude reaction mixture using column chromatography or recrystallization.

4. The process of claim 3 wherein the compound of formula I and the compound of formula II are present in a mole ratio of from 1:1 to 1:2.

5. The process of claim 3, wherein the polar aprotic solvent is 1,4-dioxane and the metal triflate is scandium triflate.

6. A compound according to one of the following chemical structures, including enantiomers and diastereoisomers thereof:

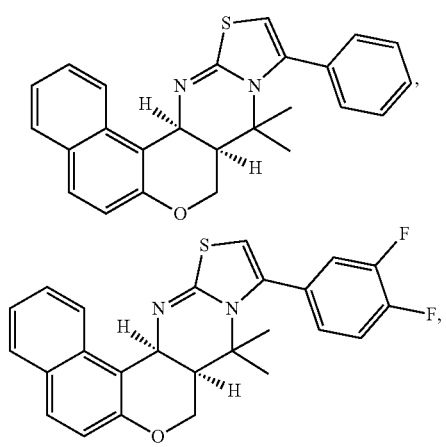

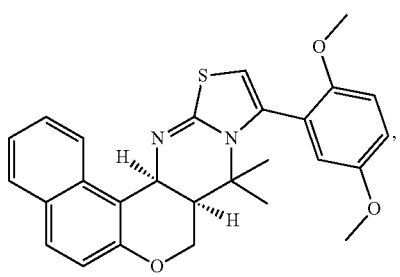

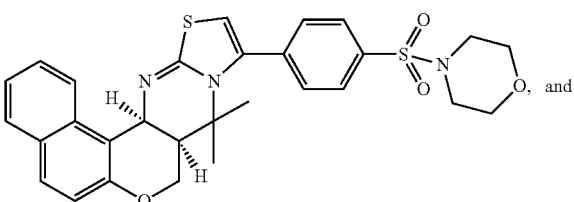

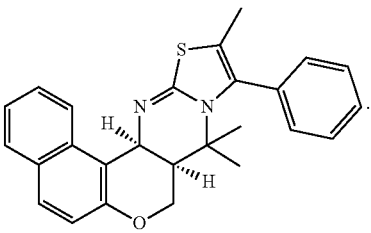

7. A pharmaceutical composition comprising one or more compounds of claim 6 as an active ingredient.

* * * * *